US012582524B2

(12) United States Patent
Van Bladel et al.

(10) Patent No.: US 12,582,524 B2
(45) Date of Patent: *Mar. 24, 2026

(54) HEART ANCHOR POSITIONING DEVICES, METHODS, AND SYSTEMS FOR TREATMENT OF CONGESTIVE HEART FAILURE AND OTHER CONDITIONS

(71) Applicant: BioVentrix, Inc., San Ramon, CA (US)

(72) Inventors: Kevin Van Bladel, San Ramon, CA (US); Lon Annest, New York, NY (US); Ernest Heflin, San Ramon, CA (US); Gilbert Mata, Jr., San Ramon, CA (US); Lawrence Crainich, San Ramon, CA (US); Brian LaRose, San Ramon, CA (US)

(73) Assignee: BioVentrix, Inc., San Ramon, CA (US)

( * ) Notice: Subject to any disclaimer, the term of this patent is extended or adjusted under 35 U.S.C. 154(b) by 104 days.

This patent is subject to a terminal disclaimer.

(21) Appl. No.: 18/444,241

(22) Filed: Feb. 16, 2024

(65) Prior Publication Data

US 2024/0245513 A1 Jul. 25, 2024

Related U.S. Application Data

(60) Division of application No. 16/744,759, filed on Jan. 16, 2020, now Pat. No. 11,903,834, which is a continuation of application No. 14/473,556, filed on Aug. 29, 2014, now Pat. No. 10,575,953.

(60) Provisional application No. 61/872,568, filed on Aug. 30, 2013.

(51) Int. Cl.
*A61F 2/24* (2006.01)
*A61B 17/00* (2006.01)

*A61B 17/04* (2006.01)
*A61B 90/00* (2016.01)

(52) U.S. Cl.
CPC ........ *A61F 2/2487* (2013.01); *A61B 17/0401* (2013.01); *A61B 2017/00243* (2013.01); *A61B 2017/0417* (2013.01); *A61B 2017/0464* (2013.01); *A61B 2090/064* (2016.02)

(58) Field of Classification Search
CPC ............... A61F 2/2487; A61B 17/0401; A61B 2090/064; A61B 2017/00243; A61B 2017/0417; A61B 2017/0464; A61B 2017/0409; A61B 2017/0411; A61B 2017/0488; A61B 2017/049
See application file for complete search history.

(56) References Cited

U.S. PATENT DOCUMENTS

2005/0251210 A1* 11/2005 Westra ............... A61B 17/0469
606/232

* cited by examiner

*Primary Examiner* — Ashley L Fishback
(74) *Attorney, Agent, or Firm* — Nixon & Vanderhye P.C.

(57) ABSTRACT

A heart anchor tensioning device includes a main body and an elongated shaft. A tension member or tether through a lumen of the elongated shaft allows the shaft to advance over the tension member and within a body while the main body is positioned outside of the body. The device includes an anchor coupling mechanism that is configured to engage a heart anchor and move the heart anchor into engagement with a first wall of the heart. The anchor coupling mechanism is to lock the heart anchor to inhibit proximal movement of the heart anchor along the tension member. The device further includes a tension indicating mechanism that provides an indication of a force being applied to the heart anchor by the device.

18 Claims, 23 Drawing Sheets

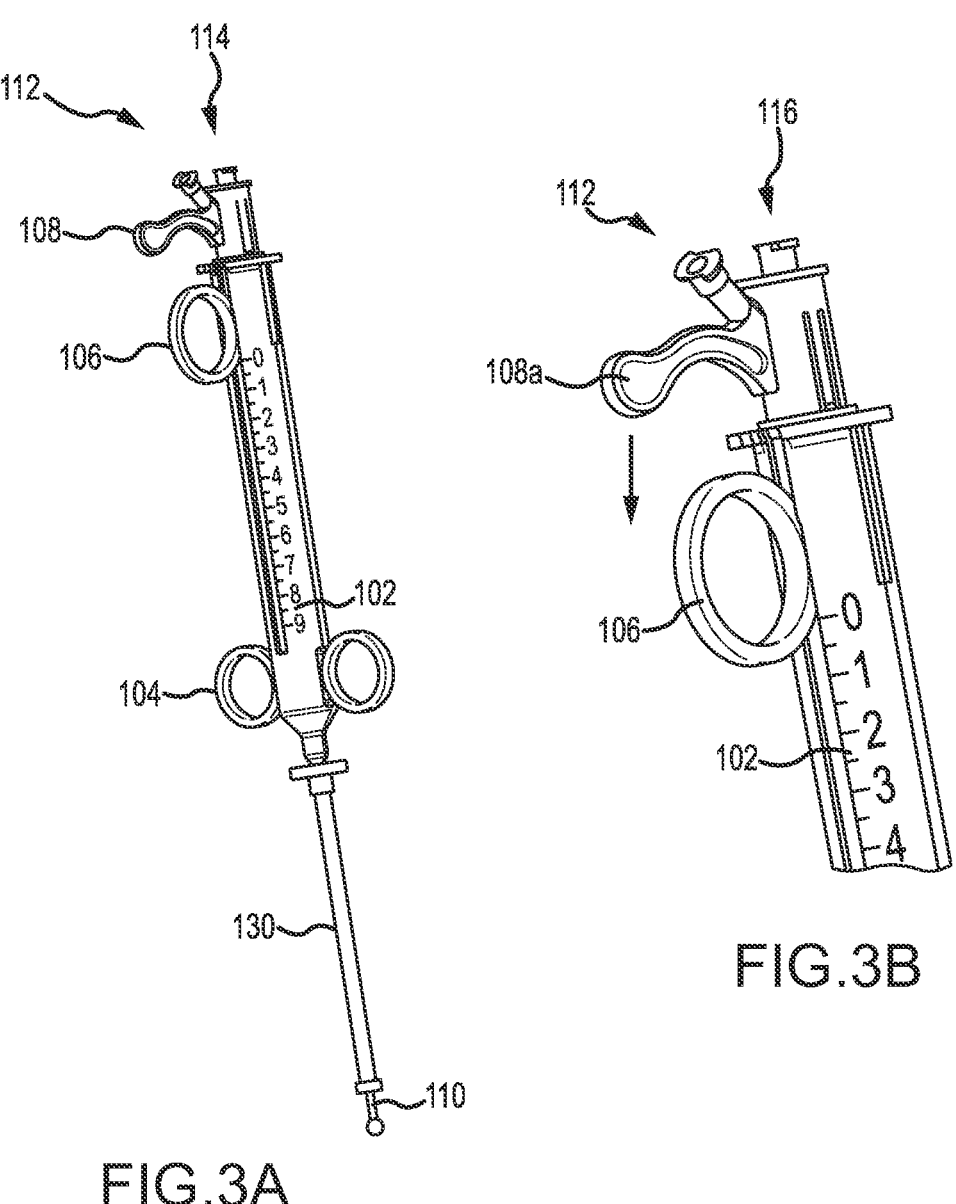
FIG.3A
FIG.3B
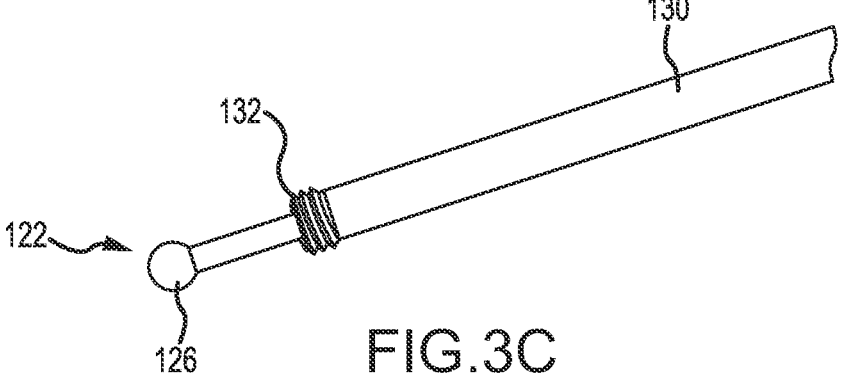
FIG.3C

908

909

910

911

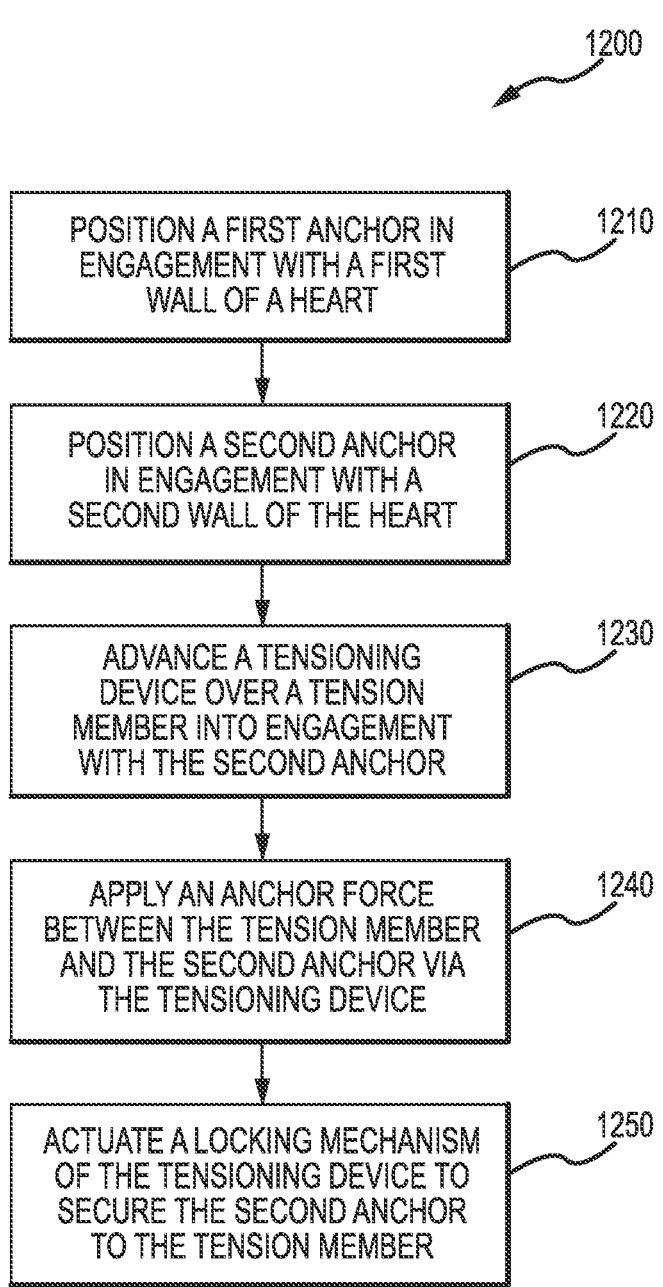

1200

POSITION A FIRST ANCHOR IN ENGAGEMENT WITH A FIRST WALL OF A HEART — 1210

POSITION A SECOND ANCHOR IN ENGAGEMENT WITH A SECOND WALL OF THE HEART — 1220

ADVANCE A TENSIONING DEVICE OVER A TENSION MEMBER INTO ENGAGEMENT WITH THE SECOND ANCHOR — 1230

APPLY AN ANCHOR FORCE BETWEEN THE TENSION MEMBER AND THE SECOND ANCHOR VIA THE TENSIONING DEVICE — 1240

ACTUATE A LOCKING MECHANISM OF THE TENSIONING DEVICE TO SECURE THE SECOND ANCHOR TO THE TENSION MEMBER — 1250

FIG.12

HEART ANCHOR POSITIONING DEVICES, METHODS, AND SYSTEMS FOR TREATMENT OF CONGESTIVE HEART FAILURE AND OTHER CONDITIONS

CROSS-REFERENCE TO RELATED APPLICATIONS

This application is a divisional of U.S. patent application Ser. No. 16/744,759 (U.S. Pat. No. 11,903,834), filed Jan. 16, 2020, which is a continuation of U.S. patent application Ser. No. 14/473,556 filed Aug. 29, 2014 (U.S. Pat. No. 10,575,953), which claims priority to provisional U.S. patent application 61/872,568, filed Aug. 30, 2013, the entire disclosures of each application are incorporated by reference.

BACKGROUND OF THE INVENTION

The present invention is related to improved medical devices, systems, and methods, with many embodiments being particularly useful for reducing the distance between two points in tissue in a minimally or less invasive manner. Specific reference is made to the treatment of a failing heart, particularly the alleviation of congestive heart failure and other progressive heart diseases. The provided devices, systems, and methods will often be used so as to resize or alter the geometry of a ventricle in a failing heart, such as by reducing its radius of curvature through the process of excluding a portion of the circumference from contact with blood, and thereby reduce wall stress on the heart and improve the heart's pumping performance. Although specific reference is made to the treatment of congestive heart failure, embodiments of the present invention can also be used in other applications in which tissue geometry is altered.

Exemplary embodiments described herein provide implants and methods for alleviating congestive heart failure and other progressive diseases of the heart. Congestive heart failure may for example, be treated using one or more implants which are selectively positioned relative to a first wall of the heart (typically an interventricular septum), and another wall of the heart so as to exclude scar tissue and limit a cross sectional area, or distance across a ventricle. Functional deterioration of the heart tissues may be inhibited by decreasing a size of the heart chamber and/or approximating tissues so that stress on the tissues is limited. Implant locations and overall chamber remodeling achieved by placement of a series of implants may be determined so as to provide a beneficial volumetric decrease and chamber shape.

Congestive heart failure (sometimes referred to as "CHF" or "heart failure") is a condition in which the heart does not pump enough blood to the body's other organs. Congestive heart failure may in some cases result from narrowing of the arteries that supply blood to the heart muscle, high blood pressure, heart valve dysfunction due to degenerative processes or other causes, cardiomyopathy (a primary disease of the heart muscle itself), congenital heart defects, infections of the heart tissues, and the like. However, in many cases congestive heart failure may be triggered by a heart attack or myocardial infarction. Heart attacks can cause scar tissue that interferes with the heart muscle's healthy function, and that scar tissue can progressively replace more and more of the contractile heart tissue. More specifically, the presence of the scar may lead to a compensatory neuro-hormonal response by the remaining, non-infarcted myocardium leading to progressive dysfunction and worsening failure.

People with heart failure may have difficulty exerting themselves, often becoming short of breath, tired, and the like. As blood flow out of the heart decreases, pressure within the heart increases. Not only does overall body fluid volume increase, but higher intracardiac pressure inhibits blood return to the heart through the vascular system. The increased overall volume and higher intracardiac pressures result in congestion in the tissues. Edema or swelling may occur in the legs and ankles, as well as other parts of the body. Fluid may also collect in the lungs, interfering with breathing (especially when lying down). Congestive heart failure may also be associated with a decrease in the ability of the kidneys to remove sodium and water, and the fluid buildup may be sufficient to cause substantial weight gain. With progression of the disease, this destructive sequence of events can cause the progressive deterioration and eventual failure of the remaining functional heart muscle.

Treatments for congestive heart failure may involve rest, dietary changes, and modified daily activities. Various drugs may also be used to alleviate detrimental effects of congestive heart failure, such as by dilating expanding blood vessels, improving and/or increasing pumping of the remaining healthy heart tissue, increasing the elimination of waste fluids, and the like.

Surgical interventions have also been applied for treatment of congestive heart failure. If the heart failure is related to an abnormal heart valve, the valve may be surgically replaced or repaired. Techniques also exist for exclusion of the scar and volume reduction of the ventricle. These techniques may involve (for example) surgical left ventricular reconstruction, ventricular restoration, the Dor procedure, and the like. If the heart becomes sufficiently damaged, even more drastic surgery may be considered. For example, a heart transplant may be the most viable option for some patients. These surgical therapies can be at least partially effective, but typically involve substantial patient risk. While people with mild or moderate congestive heart failure may benefit from these known techniques to alleviate the symptoms and/or slow the progression of the disease, less traumatic, and therefore, less risky therapies which significantly improve the heart function and extend life of congestive heart failure patients has remained a goal.

It has been proposed that an insert or implant be used to reduce ventricular volume of patients with congestive heart failure. With congestive heart failure, the left ventricle often dilates or increases in size. This can result in a significant increase in wall tension and stress. With disease progression, the volume within the left ventricle gradually increases and blood flow gradually decreases, with scar tissue often taking up a greater and greater portion of the ventricle wall. By implanting a device which brings opposed walls of the ventricle into contact with one another, a portion of the ventricle may be excluded or closed off. By reducing the overall size of the ventricle, particularly by reducing the portion of the functioning ventricle chamber defined by scar tissue, the heart function may be significantly increased and the effects of disease progression at least temporarily reversed, halted, and/or slowed.

BRIEF SUMMARY OF THE INVENTION

The present invention generally provides improved medical devices, systems, and methods. Exemplary embodiments of the devices are described for use in reducing the distance between a region along the septum and a region of an external wall of the left ventricle of a heart in a less or minimally invasive manner. According to one embodiment, a heart anchor positioning device is provided. The heart anchor positioning device includes a main body and an elongated shaft having a proximal end that is coupled with the main body and a distal end and a lumen extending between the proximal end and the distal end. A tension member is insertable through the lumen to enable the device to be advanced over the tension member so that the distal end is insertable within a body and adjacent the heart while the main body is positioned outside of the body.

The heart anchor positioning device also includes an anchor coupling mechanism that is positioned at the distal end of the elongate shaft. The anchor coupling mechanism is configured to engage a heart anchor to move the heart anchor distally and proximally along the tension member and into engagement with a first wall of the heart so as to urge the first wall toward a second wall of the heart. The anchor coupling mechanism is also configured to lock the heart anchor to inhibit proximal movement of the heart anchor along the tension member. The heart anchor positioning device further includes a tension indicating mechanism that is configured to indicate a force being applied to the heart anchor by the device.

In some embodiments, the main body includes a locking mechanism that is actuatable by a user to lock the heart anchor to inhibit proximal movement of the heart anchor along the tension member and to unlock the heart anchor to allow proximal and distal movement of the heart anchor along the tension member. In such embodiments, the elongated shaft may include a pair of hooks. The pair of hooks may be axially moveable relative to a pin disposed at a distal end of the elongate shaft. Proximal movement of the pair of hooks relative to the pin may engage the pin with a cam component of the heart anchor to unlock the heart anchor.

In some embodiments, the tension indicating mechanism may be operable in a first mode and a second mode. In the first mode, the tension indicating mechanism may allow the device to engage the heart anchor to urge the first wall toward the second wall without indicating the force being applied by the device. In the second mode, the tension indicating mechanism may indicate the force being applied to the heart anchor by the device. In such embodiments, in the first mode, the elongated shaft may be stationary relative to the main body as the force is applied to the heart anchor by the device. In the second mode, the elongated shaft may be moveable axially relative to the main body as the force is applied to the heart anchor by the device.

Further, in such embodiments, the elongated shaft may be coupled to a secondary body that is disposed within the main body. The secondary body may engage a spring component that is positioned within the main body and that allows the secondary body to move axially within the main body in the first mode. The main body may include a button component or locking mechanism that is actuatable by a user to switch the tension indicating mechanism from the first mode to the second mode to inhibit axial movement of the secondary body within the main body. The secondary body may include indicia that indicates the force being applied to the heart anchor by the device as the secondary body is moved axially relative to the main body.

According to another embodiment, a method for securing heart anchors of a heart implant device is provided. The method includes positioning a first anchor in engagement with a first wall of the heart, where the first anchor is coupled with a tension member. The method also includes positioning a second anchor in engagement with a second wall of the heart. The second anchor is slidably coupled with the tension member so that the second anchor may slide proximally and distally along a length of the tension member. The method further includes advancing a tensioning device over the tension member so that a distal end of the tensioning device engages the second anchor while a main body of the tensioning device is positioned outside of the body. The method additionally includes applying a desired anchor force between the tension member and the second anchor via the tensioning device so that the first anchor provides a force urging the first wall toward the second wall and the second anchor provides a force urging the second wall toward the first wall. During the application of the anchor force, the tensioning device may provide an indication of the anchor force applied to the second anchor by the tensioning device. The method may additionally include actuating a locking mechanism of the tensioning device to secure the second anchor to the tension member to restrict proximal movement of the second anchor along the tension member.

In some embodiments, actuating the locking mechanism of the tensioning device may reconfigure the second anchor from a variable force mode that allows the second anchor to slide proximally and distally along the tension member to a set force mode that restricts proximal movement of the second anchor along the tension member. In such embodiments, actuating the locking mechanism of the tensioning device may move a pair of hooks axially relative to a pin that is positioned on a distal end of an elongated shaft of the tensioning device. Movement of the pair of hooks relative to the pin may engage the pin with a cam component of the second anchor.

In some embodiments, the method may additionally include advancing the second anchor distally along the tension member with the tensioning device in a first mode of operation, where the first mode of operation allows the tensioning device to engage the second anchor to urge the second wall toward the first wall without indicating the anchor force being applied by the tensioning device. In such embodiments, the method may also include applying the desired anchor force to the second anchor with the tensioning device in a second mode of operation, where the second mode of operation allows the tensioning device to provide the indication of the anchor force applied to the second anchor by the tensioning device. In such embodiments, the method may further include actuating a mode button or level mechanism of a main body of the tensioning device to switch the tensioning device from the first mode of operation to the second mode of operation.

In any of the embodiments, the applied anchor force may include a Ventricular Contractile Force (VCF) and an additional force of between about 2 N and about 6 N. Alternatively, the applied anchor force may include a Ventricular Contractile Force (VCF) and an additional force of between about 3 N and about 4 N.

According to another embodiment, a system for securing heart anchors of a heart implant device is provided. The system may include a tension member having a first end and a second end, a first anchor coupled with the tension member at the first end, and a second anchor slidably couplable with the tension member. The first anchor may be configured for anchoring engagement with a first wall of the heart. The second anchor may have a variable force mode that allows the second anchor to axially slide proximally and distally along the tension member and a set force mode that inhibits proximal movement of the second anchor along the tension member. The second anchor may be configured for anchoring engagement with a second wall of the heart. The system may also include a tensioning device that is configured to: engage the second anchor to apply an anchor force between the tension member and the second anchor, provide an indication of the anchor force being applied to the second anchor by the tensioning device, and switch the second anchor from the variable force mode to the set force mode and vice versa.

In some embodiments, the tensioning device may be operable in a first mode that allows the tensioning device to engage the second anchor and apply the anchor force without providing an indication of the anchor force, and operable in a second mode that allows the tensioning device to provide the indication of the anchor force applied to the second anchor by the tensioning device.

In some embodiments, the system may additionally include a tissue penetrating device that has an elongated shaft and a lumen extending between a proximal end and a distal end of the elongate shaft. A first needle may be disposed within the lumen of the elongated shaft and may be extendable therefrom between a first configuration, in which the first needle is substantially aligned with an axis of the lumen, and a second configuration, in which the first needle curves away from the axis of the lumen. A second needle may be disposed within a lumen of the first needle and extendable therefrom to penetrate the first wall or second wall of the heart.

In some embodiments, the system may additionally include a cannula or trocar through which an elongated shaft of the tensioning device is inserted to engage a distal end of the tensioning device with the second anchor while a main body of the tensioning device remains positioned outside the body. In such embodiments, the elongated shaft may include a lumen through which the tension member is insertable to allow the tensioning device to be advanced over the tension member through the cannula or trocar. In some embodiments, the tensioning device may include indicia that indicates the force being applied to the second anchor by the tensioning device.

BRIEF DESCRIPTION OF THE DRAWINGS

The present invention is described in conjunction with the appended figures:

FIGS. 3A-3C illustrate the tissue penetrating device of FIG. 1 with an inner and outer needle retracted within an elongate shaft.

6

Figures 7A, 7B:
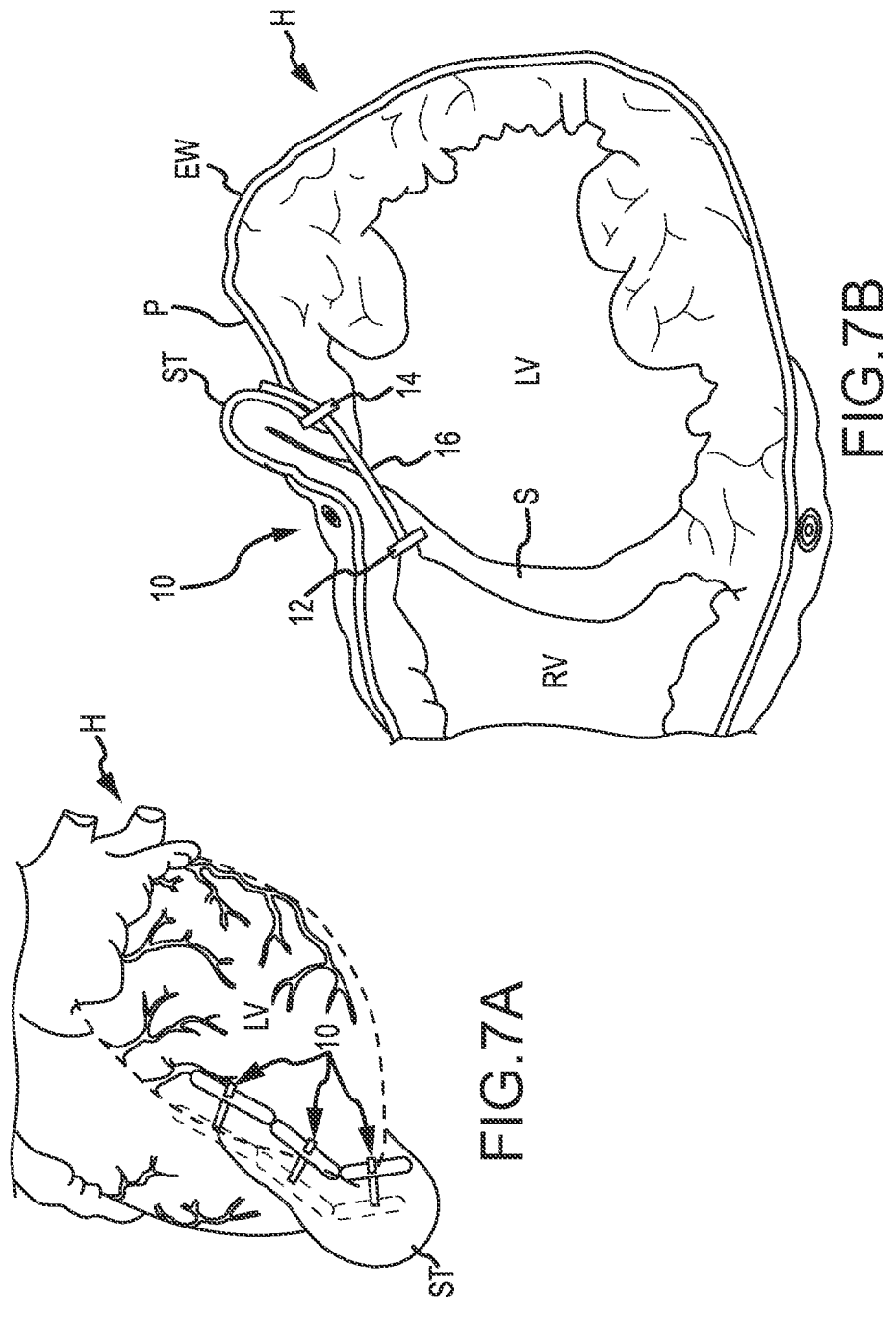
FIG. 7A illustrates a reconstructed left ventricle using a series of implanted anchors so as to mitigate the deleterious effects of congestive heart failure.
FIG. 7B illustrates a cross-sectional view of the heart of FIG. 7A, showing a reduction in the size of the left ventricle effected by one of the implants.
Figure 7C:
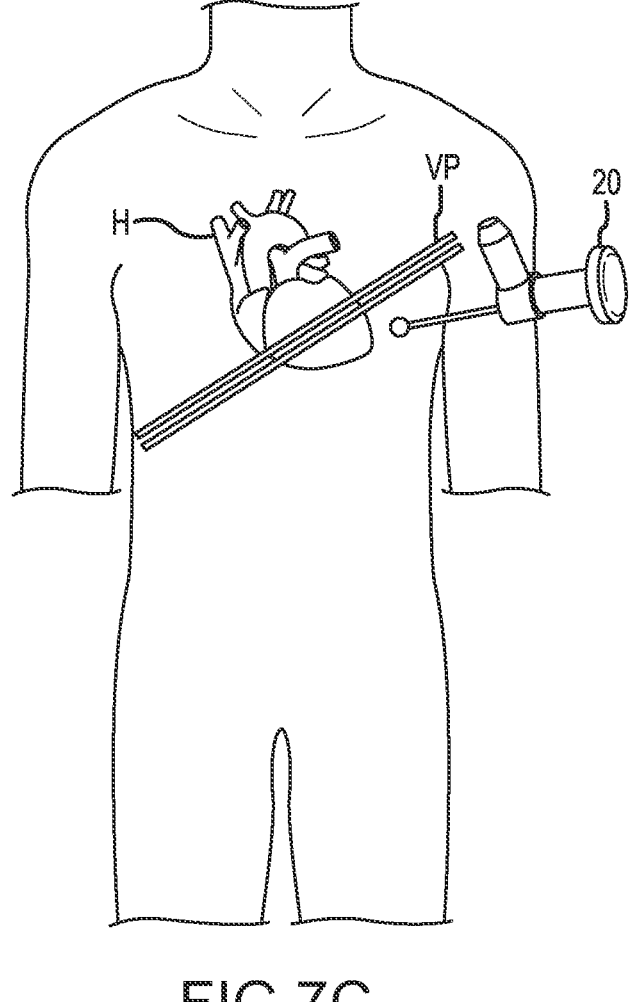
Figure 7D:
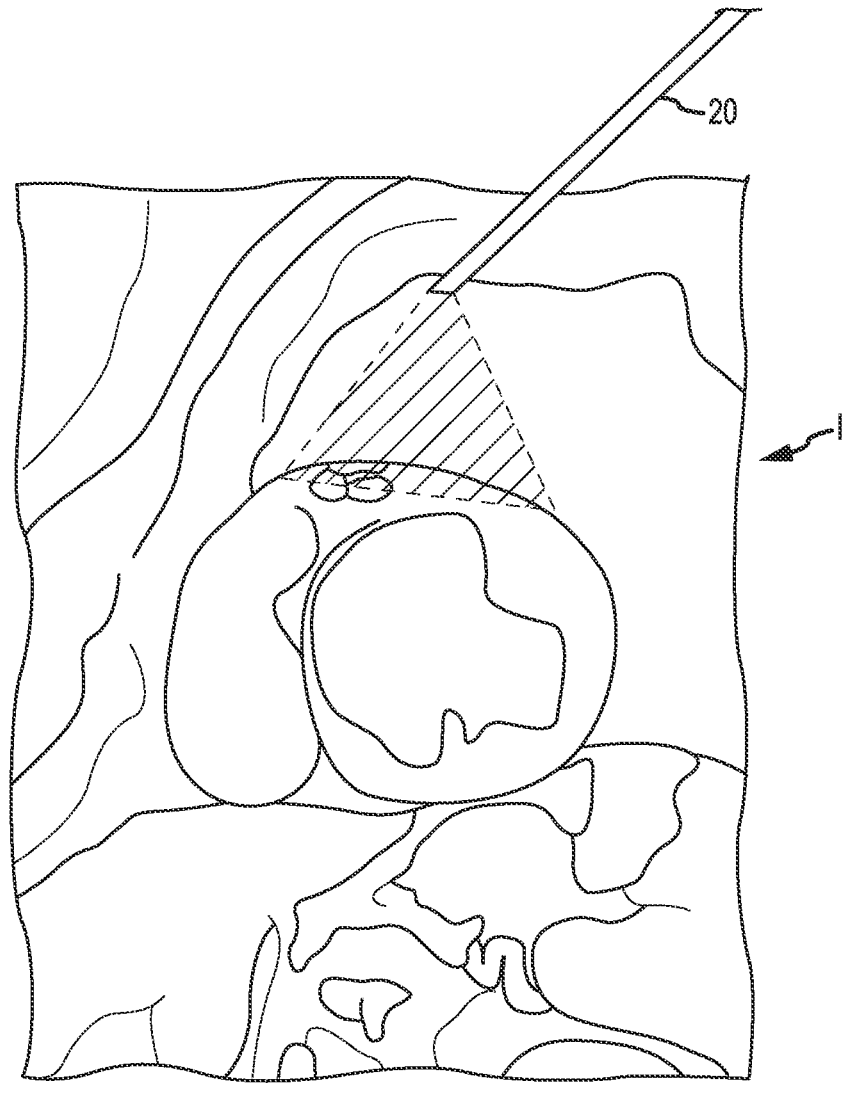

FIGS. 7C and 7D illustrate minimally invasive access to and endoscopic imaging of a pericardium of the heart.

Figure 7E:
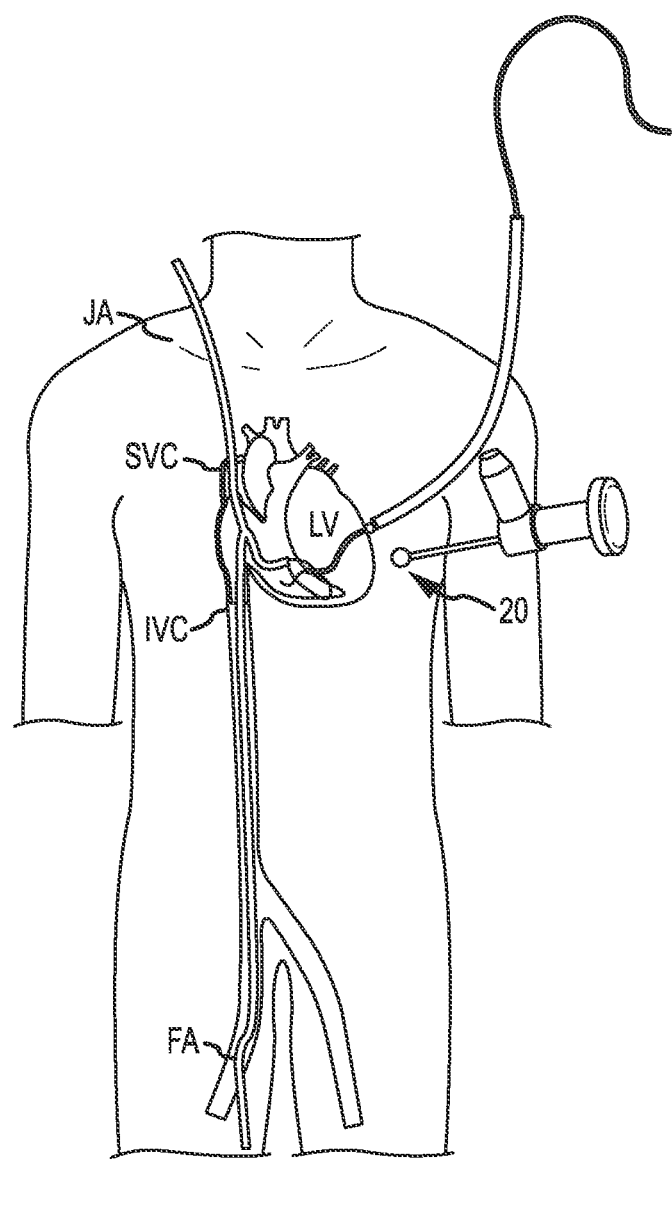

FIG. 7E illustrates joining of a femoral access tool path through the right atrium and an endoscopic trans-epicardial access tool path by snaring a guidewire within the right ventricle of the heart.

Figure 8A:
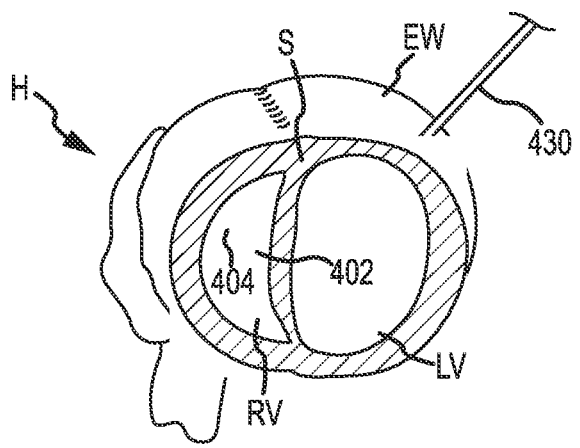

FIG. 8A illustrates a trocar or shaft positioned adjacent an external wall of a heart in a treatment for congestive heart failure.

Figure 8B:
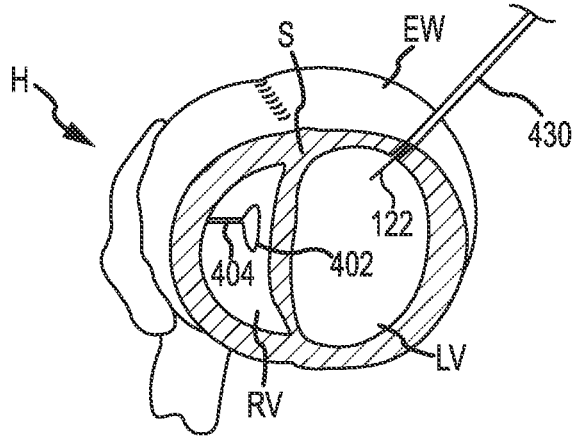

FIG. 8B illustrates an inner needle penetrating through the external wall of the heart in the congestive heart failure treatment.

Figure 8C:
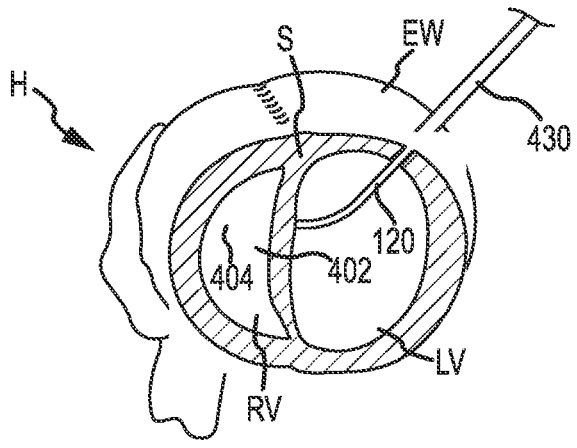

FIG. 8C illustrates an outer needle being positioned adjacent the septal wall of the heart in the congestive heart failure treatment.

Figure 8D:
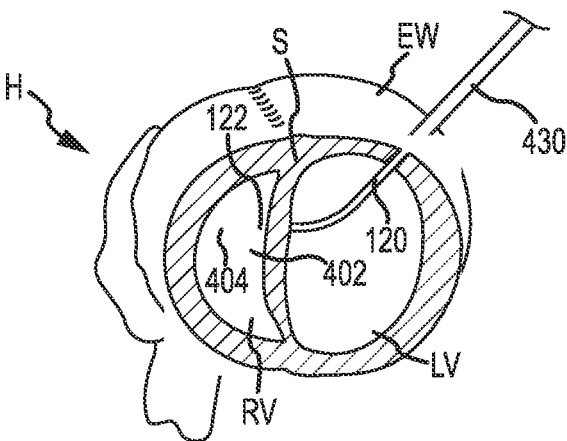

FIG. 8D illustrates the inner needle penetrating through the septal wall of the heart in the congestive heart failure treatment.

Figure 8E:
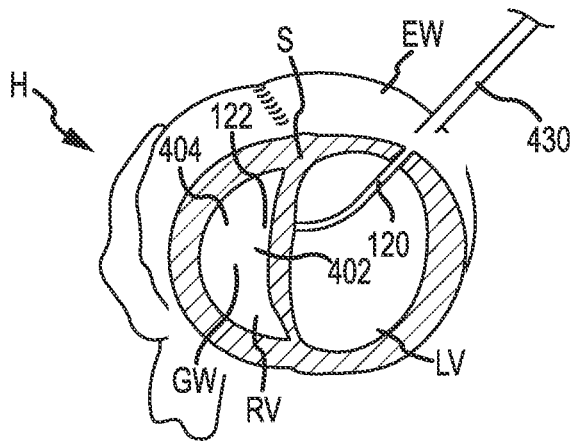

FIG. 8E illustrates a guidewire being inserted into the right ventricle of the heart so as to be snared by a snare device and join paths of the guidewire and snare device in the congestive heart failure treatment.

Figure 8F:
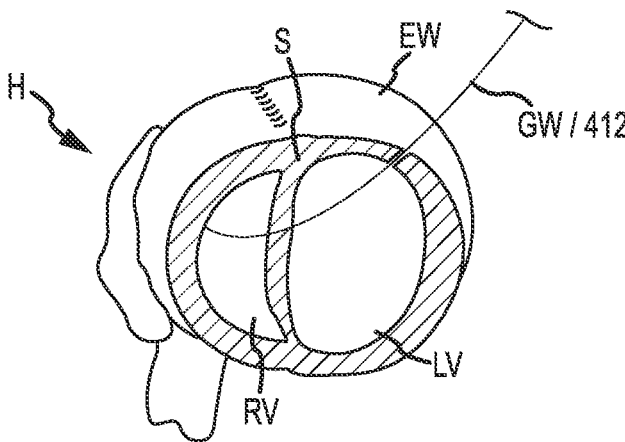

FIG. 8F illustrates the joined paths of the guidewire and snare device in the congestive heart failure treatment.

Figure 8G:
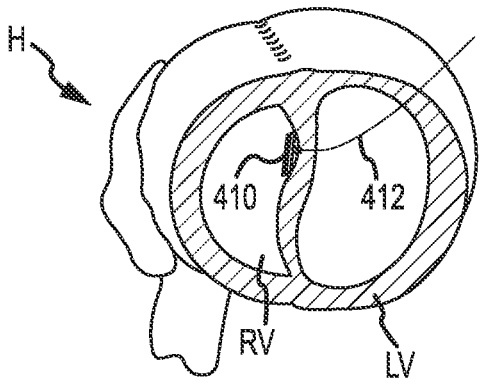

FIG. 8G illustrates a septal anchor positioned adjacent the septal wall and a tension member extending through the septal wall and external wall in the congestive heart failure treatment.

Figure 8H:
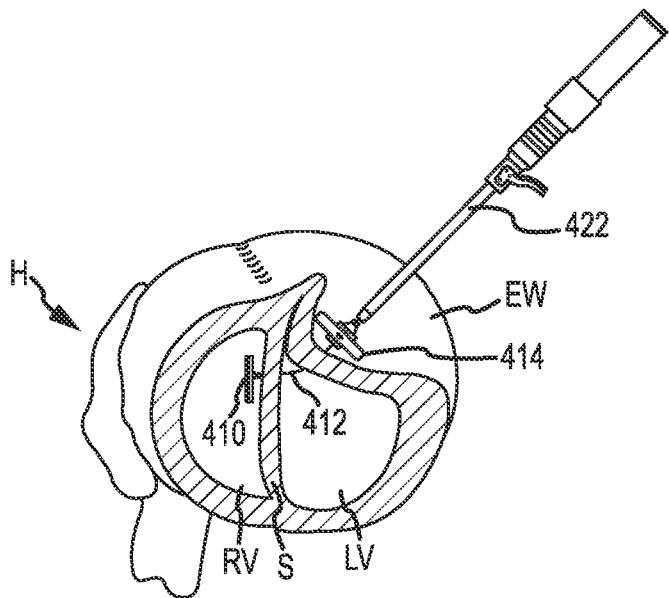

FIG. 8H illustrates an epicardial anchor application device being used to slide an epicardial anchor distally along the tension member and adjacent the external wall of the heart in the congestive heart failure treatment.

Figure 8I:
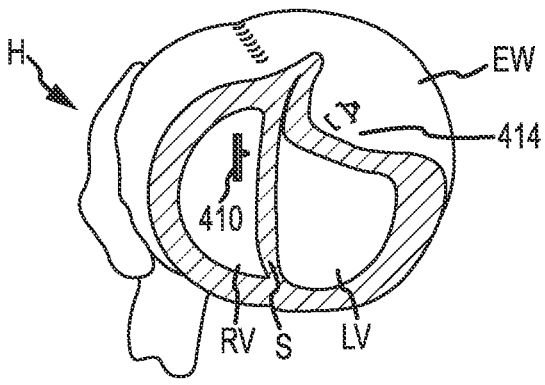

FIG. 8I illustrates the septal anchor and epicardial anchor being used to reconfigure the shape of the heart and the volume of the left ventricle in the congestive heart failure treatment.

Figure 9A:
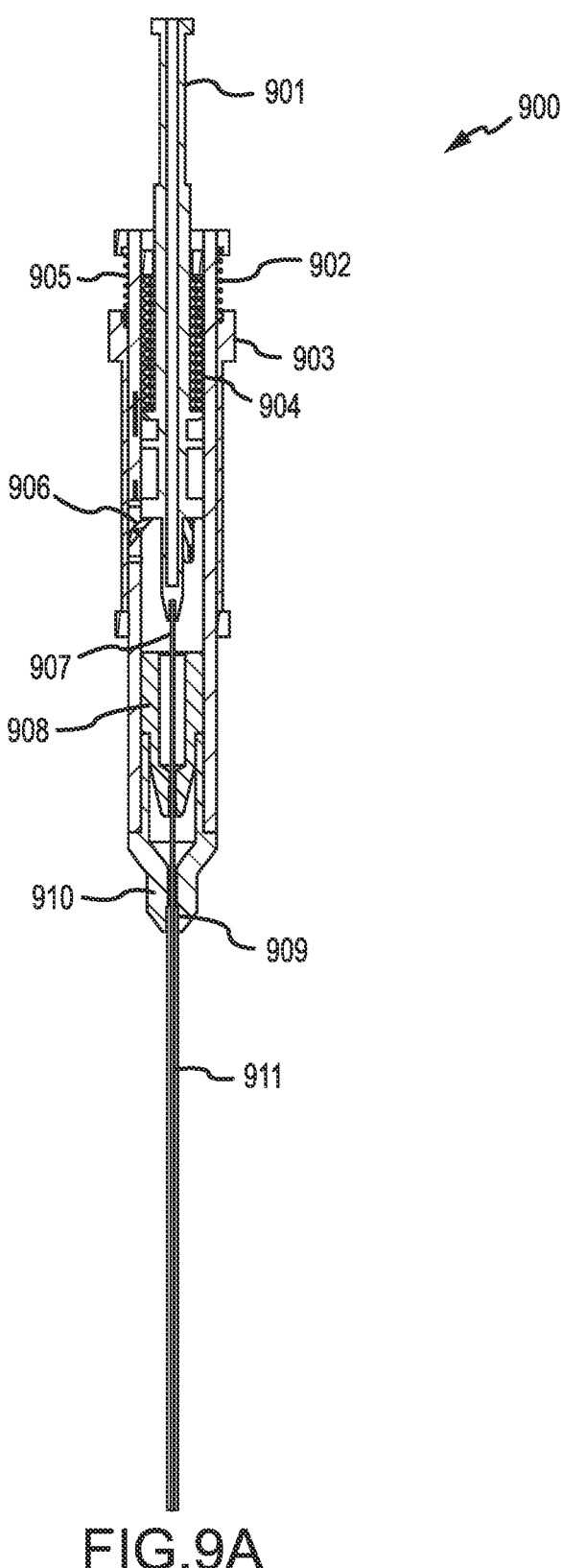

FIG. 9A illustrates a cross section view of a tissue penetrating device having a spring actuated triggering mechanism according to an embodiment.

FIGS. 9B-E illustrate enlarge cross sectional views of the tissue penetrating device of FIG. 9A.

FIGS. 10A-E illustrate an embodiment of an epicardial anchor application device.

FIGS. 11A-D illustrate an embodiment of an exemplary epicardial anchor.

FIG. 12 illustrates a method for securing heart anchors of a heart implant device.

In the appended figures, similar components and/or features may have the same numerical reference label. Further, various components of the same type may be distinguished by following the reference label by a letter that distinguishes among the similar components and/or features. If only the first numerical reference label is used in the specification, the description is applicable to any one of the similar components and/or features having the same first numerical reference label irrespective of the letter suffix.

DETAILED DESCRIPTION OF THE INVENTION

The present invention generally provides improved medical devices, systems, and methods. Exemplary embodiments of the devices are described for use in reducing the distance between a region along the septum and a region of an external wall of the left ventricle of a heart in a less or minimally invasive manner. Hence, embodiments of the tools and methods described herein may find specific use in the treatment of congestive heart failure and other progressive heart diseases by reconfiguring abnormal heart geometry that may be contributing to heart dysfunction. For congestive heart failure therapies, perforating both the exterior wall and the septum from an epicardial approach can provide significant benefits in control over the locations of implant deployments, thereby effectively enhancing the resulting reshaping of the ventricular chamber. Despite this largely epicardial approach, there are surprising benefits to guiding deployment of the implant from along both the epicardial access path and another access path into and via an access path through the right ventricle. This additional right atrial access path into the heart may be via the superior vena cava, the inferior vena cava, the right atrial appendage, or the like, and the pathways may be joined together by coupling of a snare to a guidewire or the like within the right ventricle, the right atrium, the right pulmonary artery, or the like. While a variety of tools will be described herein for providing access pathways, for joining pathways together within the heart, for deploying implants, for maintaining hemostasis, and the like, it should be recognized that alternative embodiments may employ additional or alternative structures, some of which may be off-the-shelf, and some of which may be new structures configured particularly for use in the advantageous therapies described herein.

Joining pathways may be accomplished by using a guidewire and snare device. To join the pathways, the guidewire is often inserted through the external wall and septal wall of the heart. The external wall and/or septal wall are often composed of relatively tough scar tissue, which makes insertion of the guidewire through these walls relatively challenging. For example, relatively thin and long needles (e.g., 17 Gauge (0.058")) are often used to penetrate the scar tissue of the external and/or septal walls. The needles need to be relatively long to allow a physician to position the needle through a small incision, through the external wall, and through the septal wall. These thin and long needles often bend or buckle as they are pressed firmly against the tough scar tissue, which complicates the wall penetrating processes. Further, the needle insertion points for the external wall and septal wall are typically not aligned relatively to one another. Rather, the insertion points are often angled or offset from one another by some degree. As such, straight needles are often relatively difficult to work with in penetrating both the external wall and the septal wall.

The tissue penetrating device described herein is able to easily penetrate tough scar tissue while compensating for the offset insertion points of the external wall and septal wall. This is accomplished by providing a needle and sleeve combination, or a pair of needles, that are coaxially aligned and that slide relative to one another. The needle or inner needle (hereinafter the inner needle) is a small sharp needle that is used to initially penetrate the tough scare tissue of the external wall and septal wall. In initially penetrating the scar tissue, the sleeve or outer needle (hereinafter outer needle) is positioned adjacent the scar tissue and over the inner needle. In this manner the outer needle supports the inner needle and prevents or reduces bending and/or buckling of the inner needle. After the inner needle penetrates the scar tissue, the outer needle may then be advanced over the inner needle and through the tough scar tissue of the external wall or septal wall.

Further, the outer needle is made of a flexible shape-memory material, such as nitinol, that is able to bend or flex as the outer needle is advanced distally of a distal end of an elongate shaft. As such, after the outer needle is inserted through the external wall, the outer needle may be advanced distally of the external wall, which causes the outer needle to bend toward the insertion point of the septal wall, which may be offset from the insertion point of the external wall. The outer needle may be configured to have any desired degree of bend so as to accommodate patients of various shape and size. The inner needle may likewise be made of a flexible material, such as nitinol, to allow the inner needle to be advanced within a lumen of the outer needle without altering the bent or flexed configuration of the outer needle. The outer and inner needle may be positioned adjacent a desired insertion point on the septal wall and the inner needle may be advanced distally of the outer needle and through the septal wall. A guidewire may then be inserted through a lumen of the inner needle, through the external wall and septal wall, and into a chamber of the heart for snaring and joining insertion paths as described herein.

For convenience in describing the embodiments herein, the sleeve or outer component is referred to herein as an outer needle. It should be realized, however, that the outer component is not limited to needles and that the outer component may be a sleeve, catheter, elongate shaft, or tube that is configured to track over the inner needle and bend or flex as described herein. In some embodiments, however, the outer component may be a needle that is capable to some degree of insertion through tissue with or without the inner needle.

In some embodiments, an epicardial anchor application tool or device may be used to facilitate the engagement of the septal and external walls of the heart and to lock an epicardial anchor about a tether or tension member with the septal and external walls in engagement. The epicardial anchor application tool or device may include a force gauge or tension indicating mechanism/member that provides an indication to a user of a force that is being applied to the epicardial anchor during engagement of the septal and external walls. The force gauge allows an appropriate amount of force to be applied to the anchor to engage the heart walls without risking damage to the heart walls from over-tensioned heart anchors. In this manner, proper healing of the heart tissue may be encouraged or promoted.

The epicardial anchor application tool or device may be inserted over a tether and into contact with the epicardial anchor. The epicardial anchor application tool or device may be configured to move the epicardial anchor proximally and distally along the tether and into engagement with the external wall. As the epicardial anchor application tool or device is moving the epicardial anchor distally along the tether, the epicardial anchor application tool or device may be operated in a first mode wherein an indication of the force exerted on the epicardial anchor is not provided to the user. When the septal and external walls contact one another, the epicardial anchor application tool or device may be switched to a second mode wherein an indication of the force exerted on the epicardial anchor is provided to the user. The user may then use force application feedback provided by the epicardial anchor application tool or device to appropriately tension the epicardial anchor, the tether, and a septal anchor to maintain the septal and external walls in engagement at a level that promotes healing.

The epicardial anchor application tool or device may also be used to lock the epicardial anchor in position relative to the tether and in engagement with the external wall. The epicardial anchor application tool or device may further unlock the epicardial anchor to allow for removal of the anchor and/or for the force applied by the anchor on the heart wall to be adjusted. To enable locking and unlocking of the epicardial anchor, the epicardial anchor application tool or device may include a mechanism that engages with and reconfigures the epicardial anchor between a variable force mode in which the anchor is able to slide distally and proximally along the tether, and a set force mode that restricts proximal movement of the anchor along the tether. Having generally described some embodiments, additional features of the embodiments will be recognized with reference to the figures described below.

Figure 1:
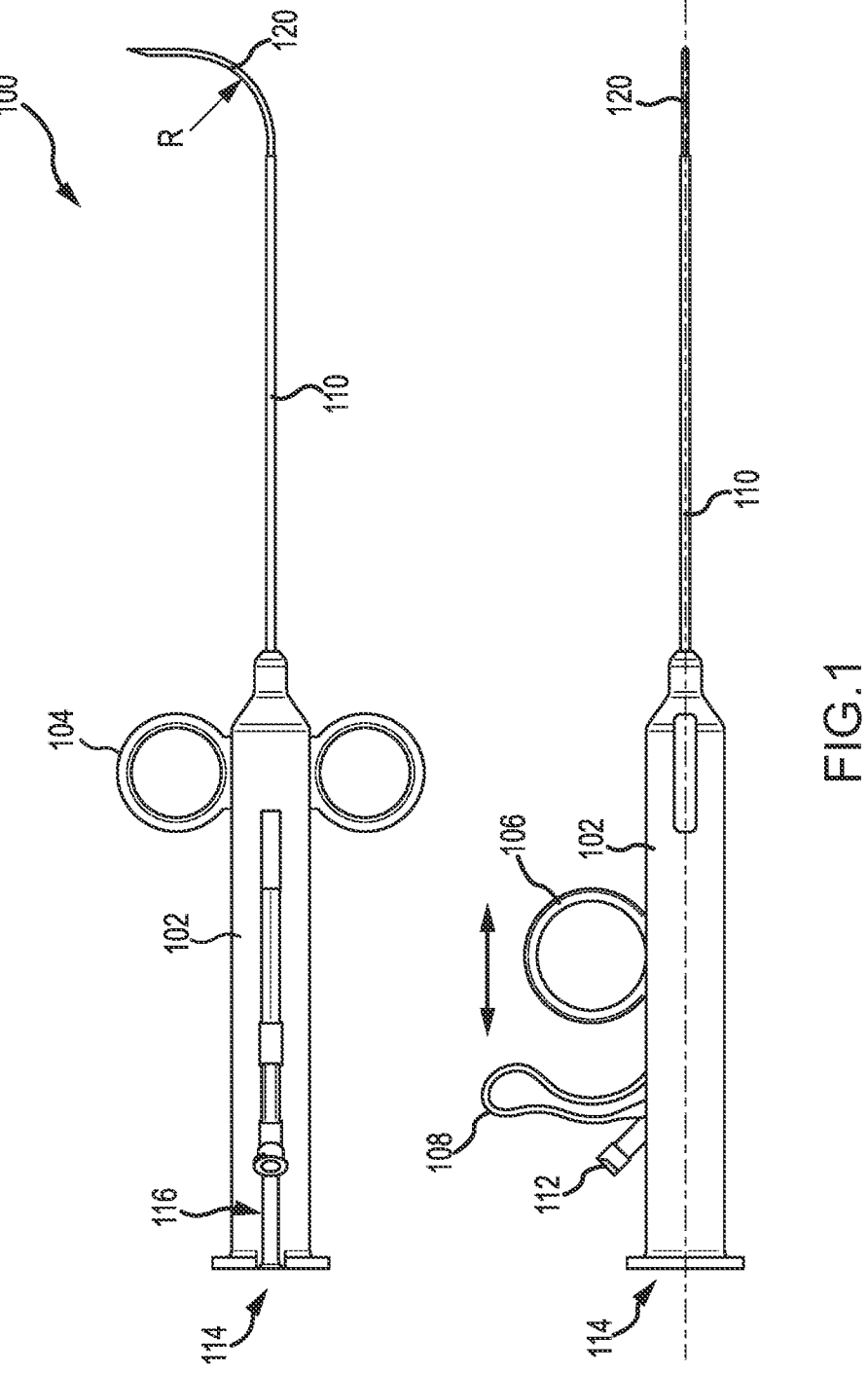
FIG. 1 illustrates a front and side view of a tissue penetrating device.

Referring now to FIG. 1, illustrated is a tissue penetrating device 100 that may be used to penetrate various tissue of the patient, such as an external wall and/or septal wall of a heart. Tissue penetrating device 100 includes a tool body 102 that may be grasped by a physician during a tissue penetrating operation. Attached to body 102 is a pair of finger guides 104 through which the physician may insert his or her fingers. A second finger guide 106, or trigger mechanism, is also slidably coupled with body 102. Finger guide 106 is able to slide axially along body 102 via track 116 to deploy and retract an outer needle 120 relative to an elongated shaft 110. A second trigger mechanism 108 is also slidably coupled with body 102. Second trigger mechanism 108 is axially movable along body 102 via track 116 to deploy and retract an inner needle (122 of FIG. 2 and the like) relative to elongated shaft 110 and outer needle 120.

Second trigger mechanism 108 is operable independently of first trigger mechanism 106 so that the inner needle 122 and outer needle 120 are independently deployable and retractable to at least some degree relative to one another. Body 102 also includes one or more ports, 112 and 114, through which a guidewire, tether or tension member, and the like may be inserted, or which may function to fluidly couple a pressure sensing fluid pathway with an external pressure monitoring or measuring device (not shown).

Outer needle 120 and inner needle 122 are disposed within a lumen of elongated shaft 110 and slidable relative thereto so as to be extendable from the lumen of elongated shaft 110 and retractable within the lumen. Further, outer needle 120 and the inner needle 122 are coaxially aligned and slidable relative to one another. Outer needle 120 is disposed over inner needle 122 with inner needle 122 being slidably disposed within a lumen of outer needle 120. Inner needle 122 is extendable distally beyond a distal end of outer needle 120 and retractable within the lumen of outer needle 120.

Figure 2:
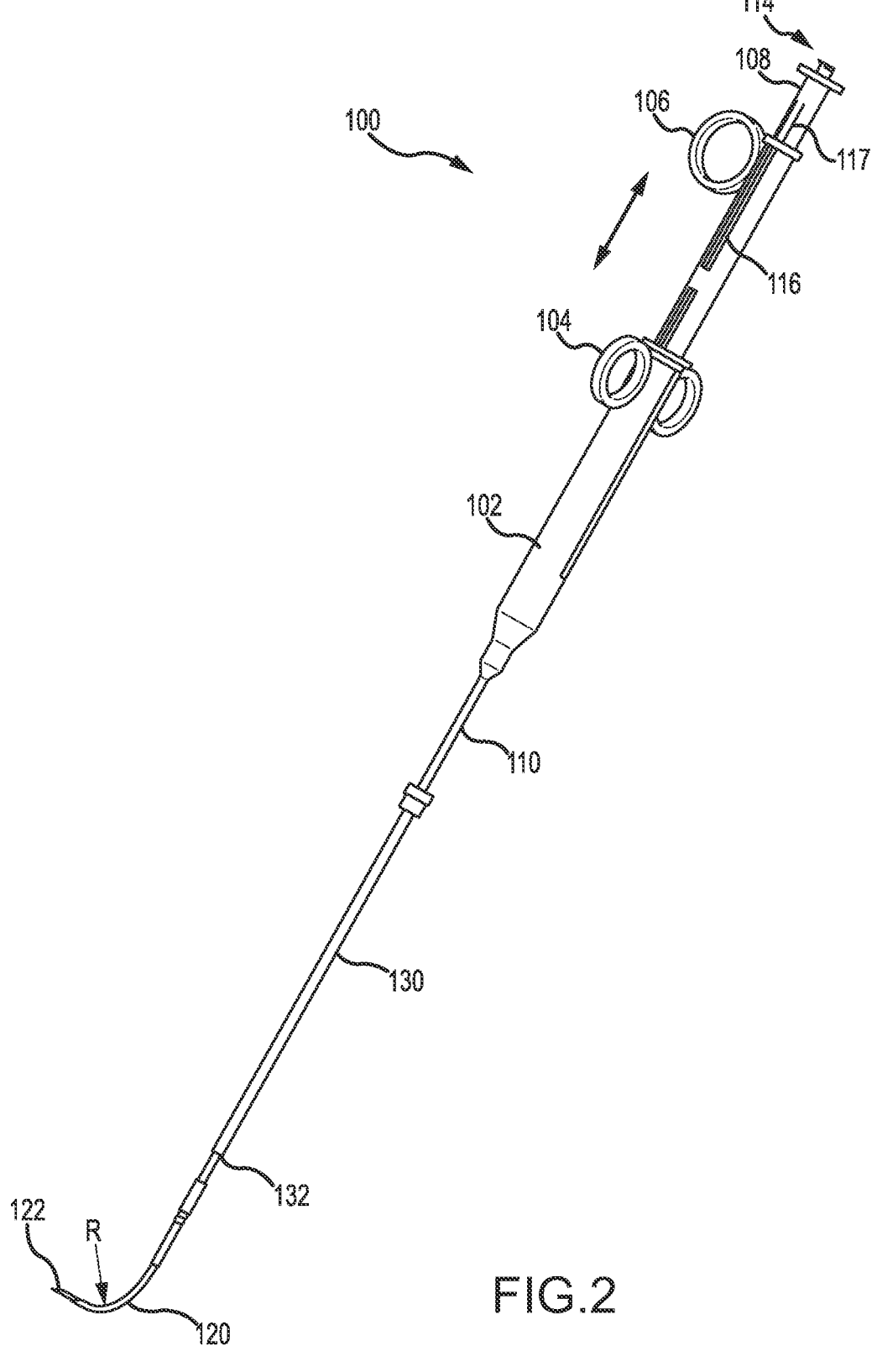
FIG. 2 illustrates a perspective view of the tissue penetrating device of FIG. 1.

FIG. 2 shows a perspective view of another embodiment of tissue penetrating device 100. FIG. 2 illustrates the finger guides 104 positioned at a proximal end of body 102. FIG. 2 further illustrates the second finger guide 106 slid proximally away from finger guides 104, which typically results in outer needle 120 and inner needle 122 being retracted within the lumen of elongated shaft 110. For illustrative purposes, however, outer needle 120 is shown being extended distally of elongated shaft 110 even though the second finger guide 106 is slid proximally away from finger guides 104. FIG. 2 additionally shows that the second trigger mechanism 108 may be coupled with a shaft or tube that is slidable within body 102 and/or within a shaft or tube of first trigger mechanism 106. The shaft or tube of the second trigger mechanism 108 and/or the shaft or tube of the first trigger mechanism 106 may include locking components 117 that help maintain the position of the second trigger mechanism's shaft or tube and/or first trigger mechanism's shaft or tube relative to one another and/or to body 102. Further, in some embodiments, the locking component 117 may help maintain a positional relationship between the inner needle 122 and the outer needle 120. For example, as the outer needle 120 is advanced distally of the distal end of elongated shaft 110, the inner needle 122 may remain in position until the distal tips of both the inner needle 122 and the outer needle 120 substantially align. Afterward, the locking component 117 may lock the first and second trigger mechanisms, 106 and 108, together so that further advancement of the outer needle 120 causes the inner needle 122 to also advance.

FIG. 2 additionally shows that an outer sleeve 130 may be slidably disposed over elongated shaft 110. Outer sleeve 130 may include a locking mechanism 132 that is couplable with a tissue anchoring device (not shown) that is positioned adjacent and/or removably coupled with tissue or an organ of the body (e.g., the heart) through which the inner needle 122 and/or outer needle 120 are to be inserted. An exemplary embodiment of a tissue anchoring device is further described in U.S. patent application Ser. No. 14/471,973 filed Aug. 28, 2014, entitled "Cardiac Tissue Anchoring Devices, Methods, and Systems for Treatment of Congestive Heart Failure and Other Conditions," the entire disclosure of which is hereby incorporated by reference, for all purposes, as if fully set forth herein.

As shown in FIGS. 1 and 2, when axially extended from elongated shaft 110, outer needle 120 may bend, flex, or curve away from an axis of elongated shaft 110's lumen. As described herein, outer needle 120 may be made of a flexible shape-memory material, such as nitinol, that is able to bend or curve by a radius R as the outer needle 120 is advanced distally of a distal end of an elongated shaft 110. The flexible material of outer needle 120 also allows the outer needle to straighten when the outer needle 120 is retracted within elongated shaft 110's lumen. When retracted within elongated shaft 110's lumen, outer needle 120 is substantially aligned with an axis of elongated shaft 110's lumen. The radius of curvature R may be selected such that when the outer needle 120 is advanced distally from a distal end of elongated shaft 110, a distal end of outer needle 120 is curved or bent away from the axis of the elongated shaft 110's lumen by between 45 and 210°, and more commonly by about 80 and 120°. In one embodiment, the radius of curvature R may be between about 10 and 38 mm. This radius of curvature range of outer needle 120 is found to be sufficient for the majority of patients.

In some embodiments, the radius of curvature R and/or degree of bend of the outer needle 120 may be dynamically adjusted. For example, when the outer needle 120 is made of nitinol, the radius of curvature R and/or bend of the outer needle 120 may be adjusted by varying the temperature of the needle. The temperature of the nitinol needle may be varied while the needle is within or external to the patient's body and may be varied automatically (e.g., the patient's body temperature may vary the needle's temperature) or in a controlled manner (e.g., via resistive heating of the needle and the like). This variation and control of the outer needle 120's shape may allow a physician to adjust the needle to fit or conform to a specific patient's geometry and/or allow a single needle to be used multiple times, such as to place multiple anchors when treating congestive heart failure.

The inner needle 122 is also made of a flexible material, such as nitinol, that allows the inner needle 122 to curve, flex, or bend by radius R as the inner needle 122 is advanced simultaneously with outer needle 120, or slid within the lumen of outer needle 120. The flexibility of the inner needle 122 prevents the inner needle 122 from straightening or otherwise affecting the radius of curvature R of outer needle 120. Stated differently, because the inner needle 122 is also made of a flexible material, the inner needle 122 may be advanced simultaneously with outer needle 120, or slid within the lumen of outer needle 120, and bent, flexed, or curved by outer needle 120 as outer needle 120 is advanced distally from elongated shaft 110. The flexibility of inner needle 122 also allows the inner needle 120 to be straightened when the inner needle 122 and/or outer needle 120 are retracted within elongated shaft 110's lumen. When retracted within the lumen of elongated shaft 110, inner needle 122 is substantially aligned with the axis of the elongated shaft 110's lumen.

The dual needle arrangement of the tissue penetrating device 100 stabilizes the inner needle 122 as the inner needle 122 is inserted through tissue of the patient. Since both the inner needle 122 and the outer needle 120, which is coaxially aligned with and positioned over inner needle 122, are positioned adjacent the patient's tissue that is to be penetrated with inner needle 122, the outer needle 120 provides a relatively rigid sheath that reinforces the inner needle 122 as the inner needle is penetrated through the patient's tissue. This configuration prevents or reduces buckling or bending of the inner needle 122 as the inner needle 122 is inserted through the patient's tissue. This configuration also allows the penetrating force of the inner needle 122 to be concentrated at a distal tip of the inner needle 122, thereby enabling the inner needle 122 to easily puncture through tough scar tissue or other tissue, which may otherwise cause bending or buckling of the inner needle 122.

Although not shown in FIGS. 1 and 2, in some embodiments the first trigger mechanism 106 and/or second trigger mechanism 108 may be spring-loaded such that actuation of the first trigger mechanism 106 and/or second trigger mechanism 108 causes a spring to rapidly fire or deploy the outer needle 120 and/or inner needle 122 across the tissue of the patient (see FIGS. 9A-E). Spring-loading the first trigger mechanism 106 and/or second trigger mechanism 108 may allow the inner needle 122 and/or outer needle 120 to easily penetrate relatively tough scar tissue or other tissue. Spring-loading of the trigger mechanisms, however, is typically not necessary and in fact may not be desired, since the support provided by the outer needle 120 allows the inner needle 122 to easily penetrate tough scar tissue and other tissue. In other embodiments, the first and/or second trigger mechanism may include a pneumatic mechanism that causes the inner needle 122 and/or outer needle 120 to be advanced via pressurized fluids.

In some embodiments, inner needle 122 may be an approximately a 21 Gauge (0.033 in) needle while outer needle 120 is a slightly larger needle, such as a 17.5 Gauge (0.054 in) needle and the like. The dimensions of the needles may be adjusted based on need, patient size, application or procedure, or otherwise as desired. In some embodiments, an outer diameter of elongated shaft 110 and/or outer sleeve 130 is smaller than about 5 mm or 7.5 mm to allow the elongated shaft 110 and/or outer sleeve 130 to be inserted through a 5 mm or 7.5 mm trocar that is positioned through a relatively small incision in the patient's skin.

In some embodiments, the distal end of elongated shaft 110 may include a joint member (see 126 of FIG. 3C and the like) that is couplable with a tissue anchoring or attachment device, such as those described in the '973 incorporated herein, that is positioned on or adjacent tissue to be penetrated with inner needle 122. The joint member 126 may allow the elongated shaft 110 and body 102 to be aligned relative to the tissue anchoring device by some degree, such as up to about 10 and 30°. This allows the distal tip of elongated shaft 110 to be positioned adjacent the tissue to be penetrated with inner needle 122 and for the tissue penetrating device 100 to be offset so that the inner needle 122 will penetrate the tissue at a desired angle and/or so that the outer needle 120 will be positioned adjacent a desired insertion point of additional tissue after the outer needle 120 is advanced from elongated shaft 110 and flexed or curved by radius R. The joint member 126 allows the outer needle 120 and inner needle 120 to be steered posterior or anterior to the heart or so some feature of the heart. For example, the alignment of the elongated shaft 110 relative to the tissue anchoring device and heart may be adjusted so that a tip of the outer needle 120 (i.e., in a bent or straight configuration) and/or the inner needle 122 may be positioned closer to a heart's apex, base, valve, septal or exterior wall, and the like as desired. This effectively allows the outer and/or inner needle's tip to be steered within or relative to a patient's heart or other tissue as needed or desired, which facilitates in precise placement and/or penetration of the needles relative to the tissue. Steering of the outer needle 120 and/or inner needle 122 may be further facilitated via the use of an imaging device (e.g., a thoracoscope, fluoroscope, and the like).

In one embodiment, when the tissue penetrating device 100 is used for treating congestive heart failure, the tissue penetrating device 100 may be aligned so that the distal tip of elongated shaft 110 and/or outer needle 120 is positioned toward an apex of the heart, toward a base of the heart, and/or toward any other desired feature of the heart. In some embodiments, the distal tip of outer needle 120 and/or inner needle 122 may be radiopaque so that the distal tip is easily identifiable via an imaging device (e.g., a thoracoscope, fluoroscope, and the like). Further, the locking mechanism 132 of outer sleeve 130 may couple the elongated shaft 110 with the tissue anchoring device and the joint member 126 may allow some degree of movement off-axis of the elongated shaft 110 relative to the tissue anchoring device as further described in the '973 incorporated herein.

In still other embodiments, the distal tip of the outer needle 120 and/or inner needle 122 may include a fluid pathway that allows a physician to monitor or measure pressure within the patient's body, such as within a chamber of the heart. Monitoring or measuring pressure may allow the location of the tip of the needle within the patient's body to be determined. In other embodiments, the distal tip of the needle 120 and/or inner needle 122 may include a pressure transducer that allows a pressure within the patient to be measured or determined as either or both needles are inserted through tissue of the patient and/or within one or more chambers within the body. For ease in describing the embodiments herein, the needle's pressure sensing fluid pathway, pressure transducer, and the like, will be referred to hereinafter as a pressure sensing element.

In one embodiment, when the tissue penetrating device 100 is used for treating congestive heart failure, the pressure sensing element (e.g., fluid pathway and the like) may be used to determine when the inner needle 122 and/or outer needle 120 have penetrated through the external wall of the heart, when the inner needle 122 and/or outer needle 120 are positioned within a chamber of the heart, when the inner needle 122 and/or outer needle 120 are positioned adjacent a septal wall of the heart, and/or when the inner needle 122 has penetrated through the septal wall and is positioned within the right ventricle of the heart. For example, the pressure sensing element may be used to measure or monitor left ventricle heart pressure, right ventricle heart pressure, and/or a damped pressure that corresponds to when the needle is imbedded within the wall of the heart (e.g., septum wall). The pressure sensing element may also be used to determine when the inner needle 122 and/or outer needle

120 are positioned adjacent scar tissue or contractile tissue of the heart to enable the physician to determine if the inner needle 122 and/or outer needle are adjacent a desired insertion point. In a specific embodiment, the inner needle 122 includes the pressure sensing element and the inner needle is used to sense pressure within the heart and/or elsewhere within the patient's body.

Referring now to FIGS. 3A-6B, illustrated is an embodiment of operating a tissue penetrating device 100. Specifically, FIGS. 3A-3C illustrate the first trigger mechanism 106 and the second trigger mechanism 108 being positioned in a proximal position relative to body 102 such that the inner needle 122 and outer needle 120 are fully retracted and disposed within the lumen of elongated shaft 110. In some embodiments, locking mechanism 132 may comprise threads that may be threaded with a corresponding aperture of a tissue anchoring device as described in the '973 application incorporated herein. FIG. 3B illustrates an enlarged perspective view of body 102 and several components of the device 100 and illustrates that body 102 may include indicia that facilitates in informing a physician of the deployment of the outer needle 120 and/or inner needle 122.

Figures 4A, 4B, 4C:
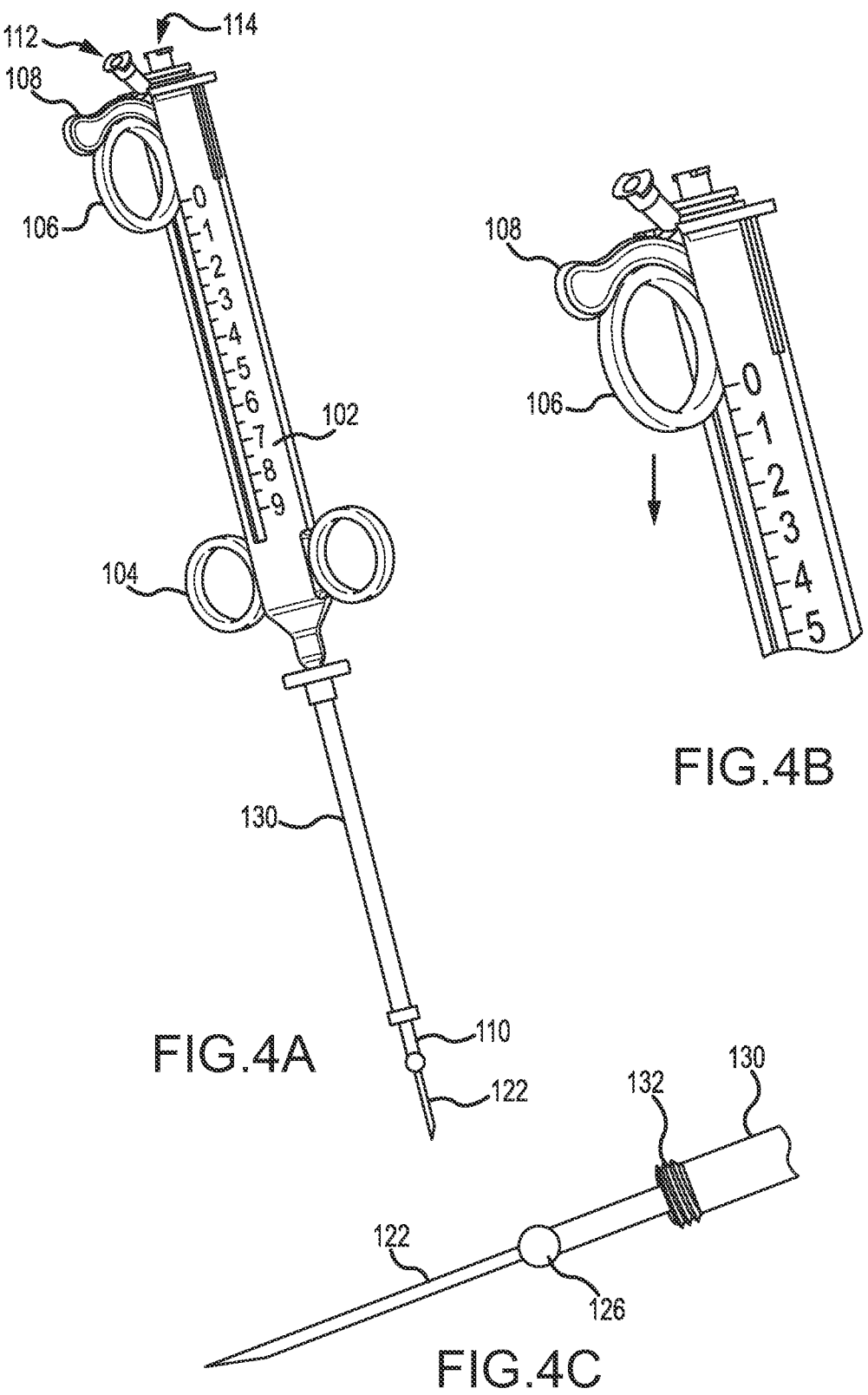
FIGS. 4A-4C illustrate the tissue penetrating device of FIG. 1 with the inner needle extending from the elongate shaft.

With the inner needle 122 and outer needle 120 fully retracted and disposed within the lumen of elongated shaft 110, the distal tip of elongated shaft 110 may be positioned adjacent the patient's tissue to be penetrated with inner needle 122, and/or the distal tip of elongated shaft 110 may be coupled with a tissue anchoring device that is positioned adjacent the patient's tissue. After the distal tip of elongated shaft 110 is positioned adjacent the patient's tissue, second trigger mechanism 108 may be slid distally along body 102 to axially advance inner needle 122 from the lumen of elongated shaft 110 and outer needle 120. The second trigger mechanism 108 may be slid distally along body 102 by placing a finger (e.g., a forefinger) within the first trigger mechanism 106 and by pressing on the second trigger mechanism 108 with another finger (e.g., a thumb). FIGS. 4A-4C illustrate the inner needle 122 extended from elongated shaft 110 after the second trigger mechanism 108 is slid distally along body 102. As shown in FIG. 4A, second trigger mechanism 108 is positioned directly adjacent the first trigger mechanism 106 after second trigger mechanism 108 is slid distally along body 102.

Figures 5A, 5B, 5C:
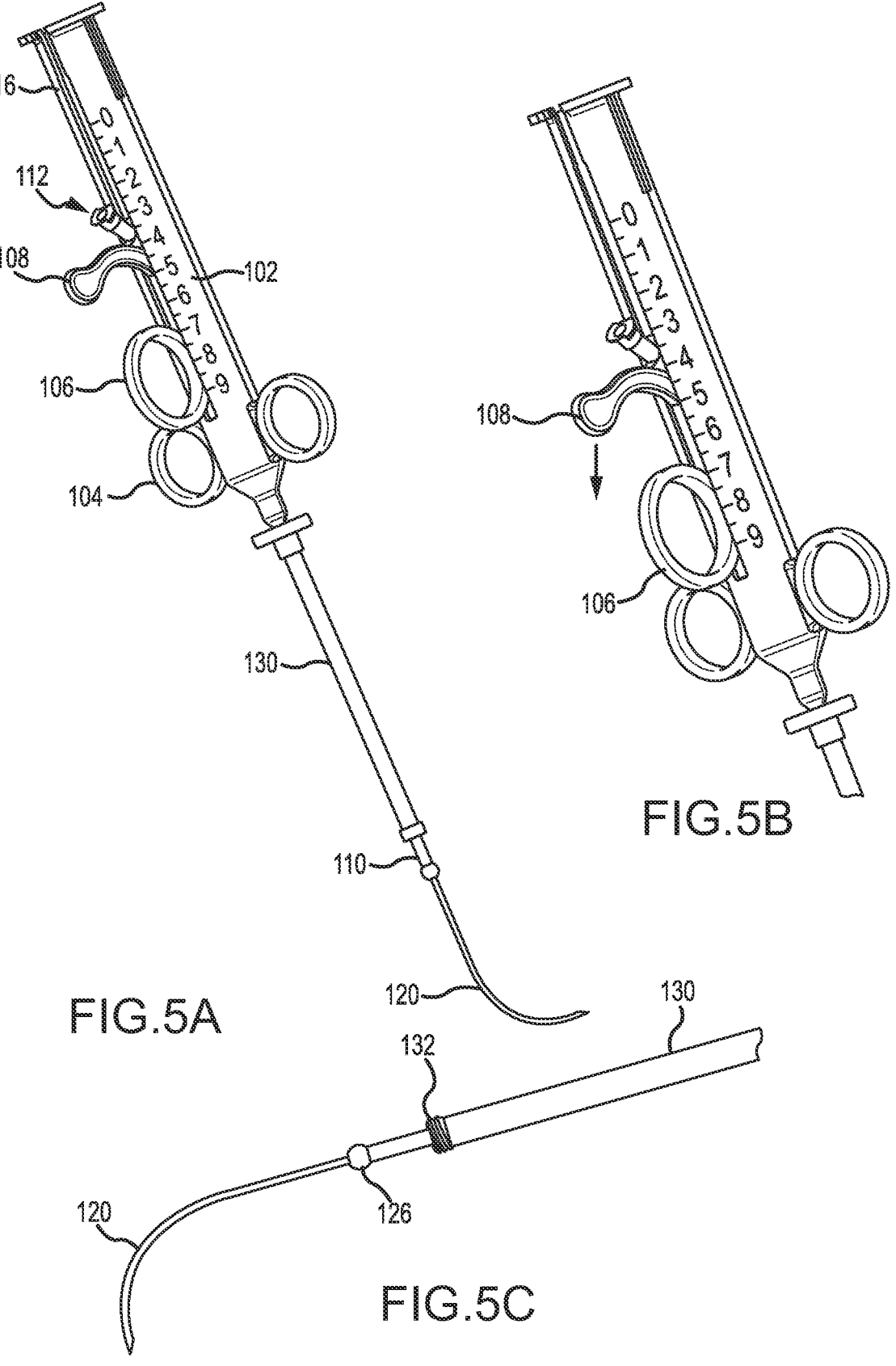
FIGS. 5A-5C illustrate the tissue penetrating device of FIG. 1 with the outer needle extending from the elongate shaft.

Advancing the inner needle 122 from elongated shaft 110 as shown in FIG. 4C causes the inner needle 122 to penetrate through tissue positioned adjacent the distal tip of elongated shaft 110. In this configuration, first trigger mechanism 106 may be slid distally along body 102 to cause the outer needle 120 to slide within the lumen of elongated shaft 110 and advance distally from elongated shaft 110. Sliding the first trigger mechanism 106 distally along body 102 may be performed by placing a finger or fingers within finger guides 104 and by pressing on first trigger mechanism 106 with another finger. FIGS. 5A-5C illustrate the outer needle 120 extending from the distal end of elongated shaft 110 after the first trigger mechanism 106 is slid distally along body 102.

As shown, the inner needle 122 may be retracted within an outer needle 120 as the first trigger mechanism 106 is slid distally along body 102. Retraction of the inner needle 122 may occur automatically as the first trigger mechanism 106 is slid along body 102. For example, the inner needle 122 may remain in position as the outer needle 120 is advanced until the distal tips of the inner needle and outer needle substantially align. Afterwards, advancement of the outer needle 120 may cause the inner needle 122 to also advance so that the distal tips of the inner needle 122 and outer needle 120 remain substantially aligned. In other embodiments, the retraction of inner needle 122 may be a manual process that is performed by a physician, such as by holding the second trigger mechanism 108 in place as first trigger mechanism 106 is slid distally along body 102, or by sliding second trigger mechanism 108 proximally along body 102. As shown in FIG. 5B and as described herein, outer needle 122 bends or curves away from an axis of the lumen of elongated shaft 110 as the outer needle 120 is advanced distally away from the distal end of elongated shaft 110. The distal end of outer needle 120 may be advanced away from the distal end of elongated shaft 110 until the distal end of outer needle 120 (and the distal end of inner needle 122) is positioned adjacent tissue to be penetrated with inner needle 122. As described herein, the outer needle 120 is made of a flexible shape-memory material and has a preconfigured curved that may be configured or selected to fit or accommodate the heart geometry of a specific patient.

Figures 6A, 6B, 6C:
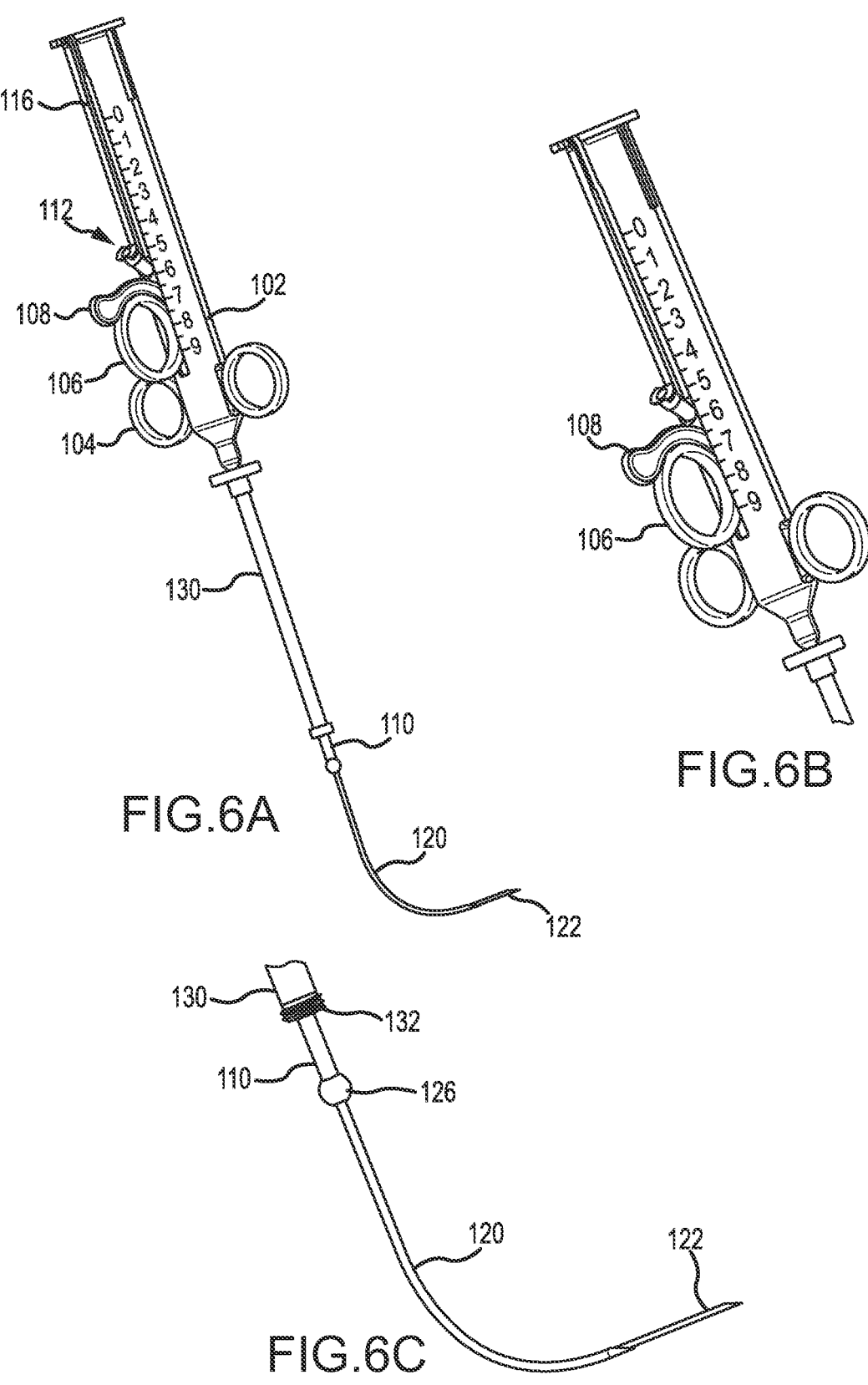
FIGS. 6A-6C illustrate the tissue penetrating device of FIG. 1 with the outer needle extending from the elongated shaft and with the inner needle extending from the outer needle.

After the distal end of the outer needle 120, and inner needle 122, is positioned adjacent tissue to be penetrated with inner needle 122, the second trigger mechanism 108 may be slid distally along body 102 to extend inner needle 122 beyond the distal end of outer needle 120 and thereby penetrate the patient's tissue. FIGS. 6A-6C illustrate the second trigger mechanism 108 being slid distally along body 102 to extend inner needle 122 so as to penetrate tissue of the patient. FIG. 6A also illustrates a track 116 within which the first trigger mechanism 106 and/or second trigger mechanism 108 may slide.

Referring now to FIGS. 7A-8I, a procedure for treating congestive heart failure using the tissue penetrating device 100 is illustrated. Specifically, FIGS. 7A and 7B illustrate a series of implants 10 implanted in a heart H so as to decrease a cross-section of a left ventricle LV. Each implant 10 generally includes a first anchor 12, a second anchor 14, and a tension member 16 coupling the anchors together. Tension in the tension member 16 is transferred from the anchors, 12 and 14, to the septum S and the external wall EW bordering the left ventricle LV so as to bring these structures into engagement, thereby effectively excluding a region of scar tissue ST from the left ventricle. In many embodiments described herein, implant 10 will be deployed by penetrating the external wall EW and septum S via a pericardium P of the heart H, and also by accessing a right ventricle RV via a right atrium. Anchors deployed within a right ventricle and/or in engagement with the septum S may sometimes be referred to herein as septal anchors, while anchors deployed along the external wall EW of the left ventricle LV may be referred to as epicardial anchors.

Referring now to FIGS. 7C and 7D and Mill image I taken along viewing plane VP schematically illustrates use of a thoracoscope or fluoroscope 20 to provide a field of view encompassing a region of the pericardium of the heart, with the region including a target site for deployment of one or more epicardial anchors and/or septal anchors of the implant system.

Referring now to FIG. 7E, joining of an access path through the right atrium to an access path through the pericardium and epicardium by snaring of a guidewire within the right ventricle under thoracoscopic/fluoroscopic guidance 20 is schematically illustrated. The right atrial access path may extend into the arterial vasculature via the femoral artery FA and inferior vena cava IVC, via the jugular artery JA via the superior vena cava, or the like. As can be understood with reference to FIG. 8A, a selected location for perforation of the external wall EW can be identified using an image from thoracoscope/fluoroscope 20, optionally in combination with an image from another imaging modality (such as a prior or contemporaneous image from an ultrasound imaging system, an MRI imaging system, an X-ray or fluoroscopic imaging system, a CT imaging system, and the like). In exemplary embodiments, a shaft 430 of an access tool having a working lumen therethrough is advanced through the epicardium of the beating heart so that a distal end of the shaft 430 is positioned adjacent the external wall EW of the heart. Shaft 430 may comprise a trocar and may have a proximal hemostasis valve at its proximal end so as to inhibit blood flow through the lumen and facilitate insertion and/or removal of elongated shaft 110 or outer sleeve 130 of tissue penetrating device 100.

A catheter 404 is inserted into the arterial vasculature via the jugular artery JA and tricuspid valve; or in other embodiments, via the femoral artery FA and inferior vena cava IVC, via the via the superior vena cava, and the like. A snare device 402, such as a wire hoop or wire basket, is positioned against the septum S at or adjacent an insertion point for inner needle 122. Snare device 402 may be positioned against septum S by using an off-the-shelf steerable catheter 404. The snare device 402 may provide a target for inner needle 122. Snare device 402 may be easily visible via fluoroscopy 20 and provide a reference point for steering the inner needle 122 and/or outer needle 120. As described herein, the distal tip of inner needle 122 and/or outer needle 120 may be radiopaque so that the distal tip of either or both needles is easily visible with a fluoroscope 20.

Shaft 430 may be positioned adjacent the external wall EW by inserting the shaft 430 through an incision between ribs of the patient, such as between the fourth and fifth intercostal space. Although not shown in the figures, in some embodiments the tissue anchoring device may be inserted through a subxiphoid incision and positioned adjacent the external wall EW. The subxiphoid incision may be relatively small, such as a two or three finger incision. The tissue anchoring device may be coupled with the external wall EW and a distal end of the shaft 430, or a distal end of elongated shaft 110, may be coupled with the tissue anchoring device to attach and/or stabilize the shaft 430 and/or elongated shaft 110 adjacent the external wall EW. The thoracoscope/fluoroscope 20 may also be inserted through the subxiphoid incision.

As shown in FIG. 8B, with the shaft 430 positioned adjacent external wall EW, the second trigger mechanism 108 may be actuated so as to advance inner needle 122 from the lumen of elongated shaft 110 and the lumen of outer needle 120 in order to penetrate the external wall EW. A pressure sensing element of inner needle 122 (e.g., fluid pathway, pressure transducer, and the like) may be used to determine that the inner needle 122 is positioned adjacent the external wall EW and/or inserted through the external wall EW and into the left ventricle LV. As shown in FIG. 8C, after the inner needle 122 is inserted through the external wall EW, the first trigger mechanism 106 may be actuated to extend the outer needle 120 distally of elongated shaft 110 and through external wall EW. The outer needle 120, and inner needle 122, may be advanced distally of elongated shaft 110 so that the outer needle 120 curves or bends away from an axis of the lumen of elongated shaft 110 and toward septum S. The inner needle 122 may be retracted within an outer needle 120 as the outer needle 120 is advanced toward septum S so as to prevent the inner needle 122 from penetrating other tissue of heart H. The outer needle 120 may be advanced until a distal end of outer needle 120 is positioned adjacent septum S. The pressure sensing element of inner needle 122 and/or of outer needle 120 may be used to determine that the distal tip of outer needle 120 is positioned adjacent septum S.

The snare device 402 and radiopaque distal tip of outer needle 120 and/or inner needle 122 may also be imaged via fluoroscope 20 to determine that the distal tip of outer needle 120 is near snare device 402. As described herein, as the outer needle 120 curves or bends as it is being distally advanced, the inner needle 122 is also forced to curve or bend along with outer needle 120. As shown in FIG. 8D, when the outer needle 120 and inner needle 122 are positioned adjacent septum S, the second trigger mechanism 108 may be actuated so as to advance inner needle 122 distally of outer needle 120 and penetrate the septal wall S. The inner needle 122 is inserted through septum S and into right ventricle RV so that the distal end of inner needle 122 is disposed within snare 402. As shown in FIG. 8D, the guidewire GW is then inserted through a lumen of inner needle 122 and into right ventricle RV. The snare device 402 may then be retracted within catheter 404 so that the snare device 402 snares the distal tip of inner needle 122 and/or guidewire GW. With the distal tip of inner needle 122 snared by snare device 402, the inner needle 122 and outer needle 120 may be retracted within elongated shaft 110 so that the guidewire GW remains snared within snare device 402.

The inner needle 122, outer needle 120, and elongated shaft 110 may then be removed from the patient's body and the guidewire GW may be pulled through catheter 404 or retracted through septum S and external wall EW to a position outside the patient's body. As shown in FIG. 8F, in this manner, an insertion path of the guidewire GW and an insertion path of the catheter 404/snare device 402 may be joined so that the guidewire GW, or another wire, extends from a first point outside the patient's body, through the external wall EW, through the septum S, through the jugular artery JA or femoral artery FA, and outside the patient's body at a second and different point. With guidewire GW extending through heart H and outside the patient's body as described above, a tension member or tether 412 may be coupled with the guidewire GW and inserted through the jugular artery JA, into the right ventricle RV, through septum S and external wall EW, and out of the patient's body. FIG. 8F illustrates that the component inserted through heart H may represent the guidewire GW, the tension member 412, or both.

A septal anchor (i.e., 410 of FIGS. 8G-8I) is coupled with a distal end of tension member 412 so that as the tension member 412 is inserted through the jugular artery JA and through heart H, the septal anchor 410 is brought into position adjacent septum S. Exemplary embodiments of septal anchors 410 and tension members 412 are described in U.S. patent application Ser. No. 13/632,104, filed Sep. 30, 2012 and entitled "Trans-Catheter Ventricular Reconstruction Structures, Methods, and Systems for Treatment of Congestive Heart Failure and Other Conditions", the entire disclosure of which is incorporated herein by reference.

FIG. 8G illustrates the septal anchor 410 positioned adjacent septum S within right ventricle RV. Tension member 412 extends from septal anchor 410 through septum S into left ventricle LV and through external wall EW. FIG. 8H illustrates that an epicardial anchor 414 is coupled with tension member 412 and slid distally along tension member 412 until the epicardial anchor 414 is positioned adjacent external wall EW. An epicardial anchor application device 422 may be used to slide epicardial anchor 414 proximally and/or distally along tension member 412 to external wall EW. The epicardial anchor application device 422 may also be used to apply tension between septal anchor 410 and epicardial anchor 414 to urge or bring the septum S and external wall EW together. The epicardial anchor application device 422 may provide an indication of the force applied by the device 422 to the epicardial anchor 414. This may allow a user to determine when an appropriate force has been applied to the anchor 414 to bring the septum S and external wall EW into engagement without risking unnecessary damage to the heart and/or anchors—e.g., the anchors pulling or tearing through the heart tissue.

The epicardial anchor application device 422 may further be used to lock or secure the epicardial anchor 414 in place about tension member 412 to prevent the epicardial anchor 414 from moving proximally along tension member 412 and to keep the septum S and external wall EW in position relative to one another. The epicardial anchor application device 422 may then be uncoupled from the epicardial anchor 414 and removed from the patient's body. An exemplary embodiment of an epicardial anchor 414 is illustrated in FIGS. 11A-D and described in the '104 application incorporated herein. An exemplary embodiment of an epicardial anchor application device 422 is illustrated in FIGS. 10A-E and described in greater detail herein below.

As shown in FIG. 8I, after the septal anchor 410 and epicardial anchor 414 are tensioned so that the septum S and external wall EW are brought together, the tension member 412 proximal to epicardial anchor 414 may be cut and discarded. The septal anchor 410 and epicardial anchor 414 may be left in position relative to septum S and external wall EW with the heart H reconfigured to reduce a volume of left ventricle LV and exclude scar tissue from the left ventricle LV. The above process may be repeated a plurality of times to position additional septal anchors 410 and/or epicardial anchors 414 about the septum S and external wall EW. The anchors may be aligned about a desired contour of the heart, such as a contour defined by scar tissue and the like. In some embodiments, the contour for placement of multiple anchors may be determined via an image of the heart and insertion points for the anchors may be calculated or measured from the image. The insertion points may then be mapped or marked on the heart, such as by using a template or pattern. In this manner, the shape of heart H and the volume of left ventricle LV may be reconfigured as desired.

In some embodiments, deployment of multiple anchors about the septum S and/or external wall EW may be accomplished using multiple access ports and trocars or cannulas, or multiple anchors may be deployed via the same access port. For example, in some embodiments the tissue penetrating device may be used to penetrate the external wall EW and/or septum S in multiple locations via the same access port. The tissue penetrating device is capable of delivering multiple penetrations via a single access port due, in part, to the bending or curving of the outer and inner needle. Further, in some embodiments the tissue penetrating device may be inserted through various incisions to penetrate the heart's tissue and deliver heart anchors, such as through incisions between ribs, subxiphoid incisions, and the like.

In another embodiment, the process illustrated in FIGS. 8A-I may essentially occur in reverse. For example, the tissue penetrating device may be inserted into the arterial vasculature via the femoral artery FA and inferior vena cava IVC, via the jugular artery JA via the superior vena cava, or the like. In such embodiments, the elongated shaft 110 may be a catheter that is easily insertable and/or steerable through the patient's arteries and into the arterial vasculature. The catheter (i.e., elongated shaft 110) may then be inserted into the right ventricle RV via the tricuspid valve and the distal tip of the catheter may be positioned adjacent the septum S.

The inner needle 122 may then be advanced distally of the catheter to penetrate through the septum S. The outer needle 120 may then be advanced through the septum S and advanced toward the external wall EW. The outer needle 120 may bend, flex, or curve as it is being advanced toward external wall EW as described herein.

A snare device 402 may be positioned adjacent the external wall EW and may provide a target for placement of the distal tip of the outer needle 120 relative to the external wall EW of the left ventricle LV. The distal tip of the outer needle 120 may be positioned adjacent the external wall EW at or near the target position defined by the snare device 402 and the inner needle 122 may be advanced distally of the outer needle 120's distal end to penetrate through the external wall EW. The inner needle 122, and/or a guidewire GW inserted through the inner needle 122's lumen, may then be snared via snare device 402 so as to join a pathway of the guidewire GW and snare device 402 as described herein. Placement of the septal anchors and/or epicardial anchors may then be performed as described above.

In some embodiments, the snare device 402 may be inserted through the external wall EW and into the left ventricle LV and the outer needle 120 may be advanced within the left ventricle LV toward the snare device 402. The outer needle 122 may be advanced within the left ventricle LV until it is able to be snared by snare device 402, after which the outer needle 120, inner needle 122, and/or guidewire GW may be snare to join access paths and deploy septal and/or epicardial anchors as described herein.

Referring now to FIGS. 9A-9E, illustrated is an embodiment of a tissue penetrating device 900 having a spring actuated triggering mechanism. FIGS. 9B-9E illustrate enlarged cross section views of the device 900 showing the various components in greater detail. Tissue penetrating device 900 may be actuated to rapidly fire or deploy an outer needle and/or inner needle across the tissue of the patient, such as across an external wall EW or septal wall S. Device 900 includes a straight needle trigger rod 901 that may be actuated by a physician to rapidly deploy an inner and/or outer needle, and more commonly only an inner needle.

Figures 9B, 9C:
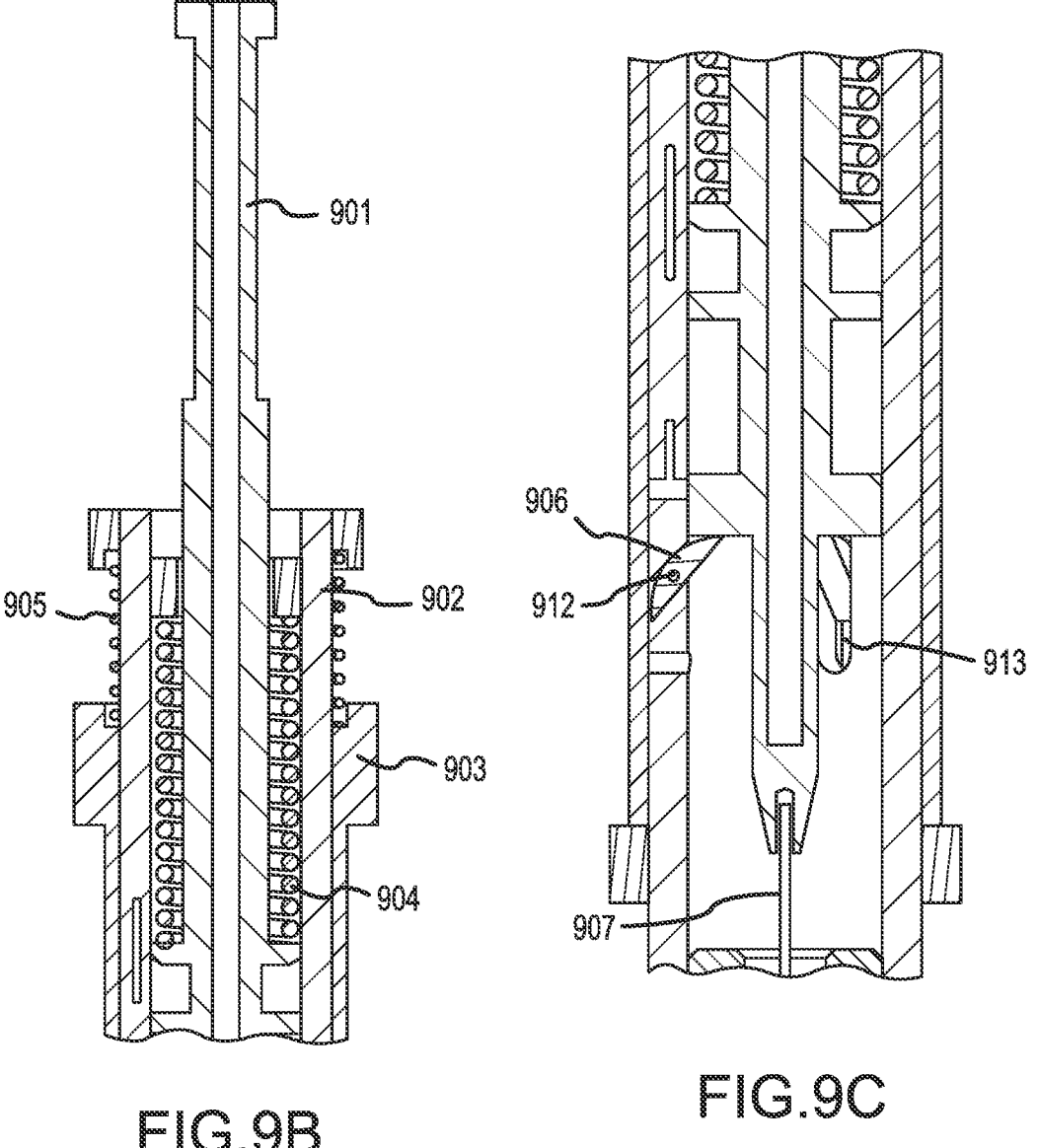
Figure 9D:
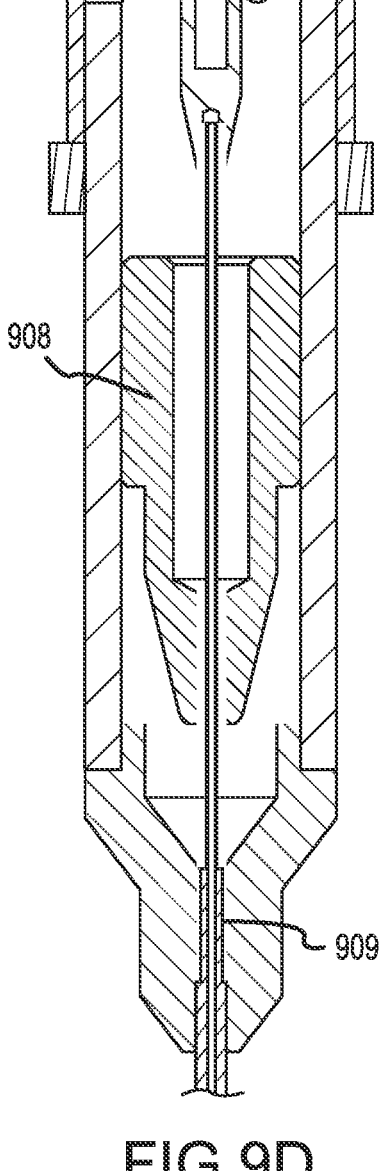
Figure 9E:
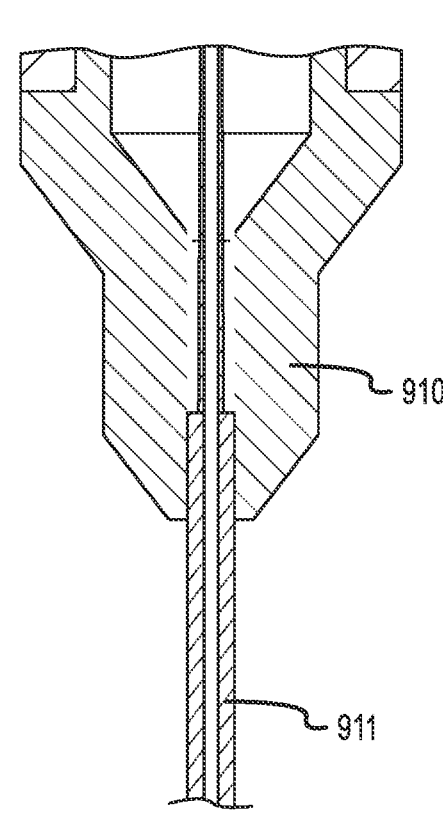

Device 900 includes an outer housing 902. Device 900 further includes a trigger release sleeve 903 that may be rotated to release trigger release tabs 906 via a window 913 (FIG. 9C) and thereby actuate trigger rod 901. In one embodiment, device 900 may include 3 trigger release tabs 906 and 3 windows 913. Device 900 additionally includes a trigger spring 904 that, upon actuation, causes trigger rod 901 to rapidly move distally relative to the other components of device 900. Device 900 also includes a spring 905 for trigger release sleeve 903. Device 900 additionally includes a straight or inner needle 907 that is rapidly fired or deployed upon actuation of trigger spring 904 and trigger rod 901. Device 900 also includes a curved or outer needle 909 and two needle inserts 908 and 910. An elongated shaft or sheath 911 is coupled with a distal end of insert 910 and includes a lumen within which outer needle 909 and inner needle 907 are coaxially aligned and slidably disposed. As shown in FIG. 9C, the trigger release tabs 906 may be pivotally coupled to housing 902 via a pivot pin 912 and may prevent distal movement of trigger rod 901 until released by rotating trigger release sleeve 903 and aligning trigger release tabs 906 with corresponding windows 913.

Rotating trigger release sleeve 903 so as to align trigger release tabs 906 with the corresponding windows 913 actuates trigger rod 901 and causes the trigger rod 901 to spring forward via trigger spring 904 until a distal end of trigger rod 901 contacts insert 908. The forward springing movement of trigger rod 901 causes inner needle 907 to rapidly deploy relative to outer needle 909 and elongated shaft 911 and thereby penetrate tissue adjacent a distal end of the elongated shaft 911 and/or outer needle 909. The trigger rod 901, trigger spring 904, and trigger release sleeve 903 may be reset for subsequent firing.

Figure 10A:
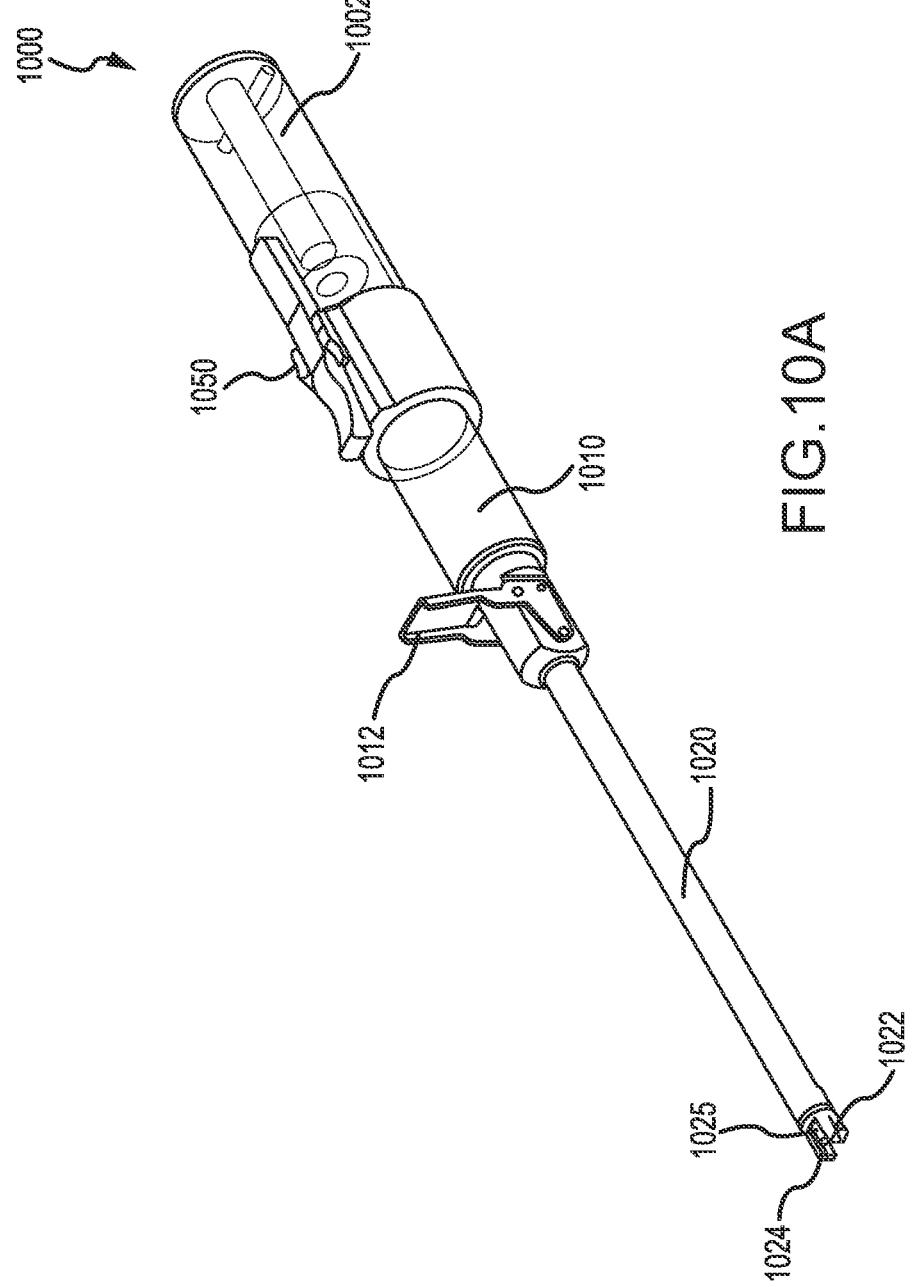

FIGS. 10A-E illustrate an embodiment of an exemplary epicardial anchor application device 1000. FIG. 10A illustrates a perspective view of the epicardial anchor application device 1000. The epicardial anchor application device 1000 includes a main body 1002 and a secondary body 1010 that is disposed within main body 1002 and axially moveable relative thereto. A spring component (1030 of FIGS. 10D & 10E) is disposed within the main body 1002 and engages a distal end of the secondary body 1010 to allow the secondary body 1010 to move axially within the main body 1002. The epicardial anchor application device 1000 includes a switch, mode button, or locking mechanism 1050 that is actuatable by a user to lock and unlock the secondary body 1010 relative to the main body 1002 as described herein.

The epicardial anchor application device 1000 further includes an elongated shaft 1020 that is coupled with and extends distally from the secondary body 1010. The shaft 1020 is configured for insertion through a trocar or cannula positioned in an incision between ribs or elsewhere of a patient to allow a pair of hooks, 1022 and 1024, at the distal end of the elongated shaft 1020 to engage with an epicardial anchor (i.e., 1155 of FIGS. 11A-D). An engagement pin 1025 is positioned between the pair of hooks, 1022 and 1024, and is configured to engage a cam spring mechanism of the epicardial anchor to lock and unlock the epicardial anchor about a tether or tension member as described hereinbelow.

In operation, the epicardial anchor application device 1000 is used to move the epicardial anchor proximally and distally along the tether or tension member and into engagement with an external wall EW of the heart. The epicardial anchor application device 1000 may then be used to apply a force to the epicardial anchor to urge the external wall EW toward and into engagement with the septum S. The pair of hooks, 1022 and 1024, and engagement pin 1025 may then be used to lock the epicardial anchor about the tether or tension member with the external wall EW and septum S in contact. The epicardial anchor application device 1000 is also configured to provide an indication of the force applied to the epicardial anchor as the external wall EW and septum S are brought into engagement.

In some embodiments, the epicardial anchor application device 1000 may be operated in a first mode and a second mode. In the first mode, the secondary body 1010 may be locked relative to the main body 1002 to allow the epicardial anchor application device 1000 to move the epicardial anchor proximally and distally along the tether without providing an indication of the force applied to the epicardial anchor. This may allow the external wall EW and septum S to be easily brought into contact since essentially the entire force applied by the epicardial anchor application device 1000 is transferred to the epicardial anchor. Stated differently, engaging the external wall EW and septum S with the epicardial anchor application device 1000 positioned in the first or locked mode may be relatively easy since the force applied to the epicardial anchor application device 1000 and/or the beating of the heart is not causing the secondary body 1010 to move axially within the main body 1002. When the external wall EW and septum S are brought into contact, the epicardial anchor application device 1000 may be switched to the second mode that allows the secondary body 1010 to move axially within the main body 1002 to provide an indication of the force being applied to the epicardial anchor by the epicardial anchor application device 1000. In this manner a user may apply an appropriate amount of tension between the epicardial anchor and a septal anchor since the applied force is displayed, indicated, provided, or otherwise made available to a user.

The applied force may be sufficient to keep the external wall EW and septum S in engagement with one another while minimizing or eliminating unnecessary damage to the heart tissue. In some embodiments, the applied force may include a Ventricular Contractile Force (VCF), or a force necessary to overcome a beating of the heart, and an additional force of between about 2 N and about 6 N. In another embodiment, the applied force may include a Ventricular Contractile Force (VCF) and an additional force of between about 3 N and about 4 N. These forces are sufficient to ensure that the external wall EW and septum S remain engaged or in contact without damaging the tissue of the heart.

Figures 10B, 10C, 10D:
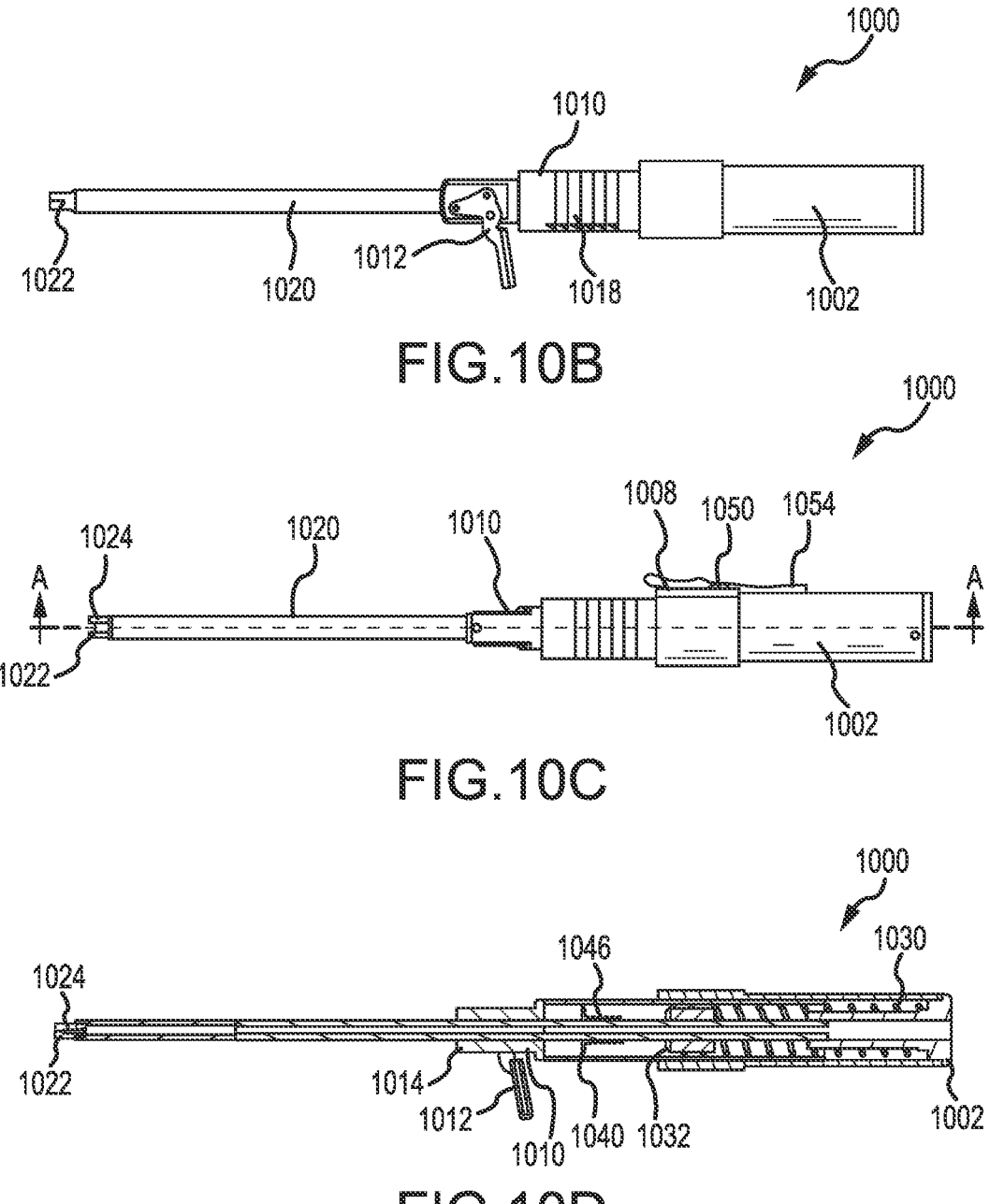

FIG. 10B illustrates a side profile view of the epicardial anchor application device 1000. FIG. 10B shows the secondary body 1010 positioned within main body 1002 and shows the elongated shaft 1020 extending distally from a distal end 1014 of the secondary body 1010. The lever mechanism 1012 is shown in a locked or engaged position in which the pair of hooks 1022 and 1024 would engage with an epicardial anchor and allow the anchor to move proximally and distally along a tether as described below. To unlock or disengage the epicardial anchor, the lever mechanism 1012 may be rotated clockwise relative to the secondary body 1010, which would result in the pair of hooks 1022 and 1024 disengaging from the epicardial anchor, thereby locking the anchor about the tether to restrict proximal movement of the anchor about the tether. FIG. 10B also shows the secondary body 1010 including indicia 1018 that provides an indication of the anchor force applied to the epicardial anchor as the secondary body 1010 moves axially within the main body 1002. The indicia 1018 may include a plurality of concentric rings or markings positioned axially along the secondary body 1010 that each indicate or display a number corresponding to an applied force (e.g., 1 N, 2 N, 3 N, and the like).

FIG. 10C illustrates another side profile view of the epicardial anchor application device 1000 with the device rotated approximately 90 degrees about a central axis. FIG. 10C illustrates many of the components of epicardial anchor application device 1000 previously described and further illustrates the locking mechanism or mode button 1050 in greater detail. Specifically, locking mechanism 1050 includes a proximal end having a boss or shaft 1054 that extends into an aperture (not shown) of the main body 1002 to lock the secondary body 1010 in position relative to the main body 1002. The locking mechanism 1050 also includes a distal end that may be pressed by a user to cause the proximal end to pivot so that the boss 1054 pivots out of the aperture of main body 1002. Pivoting the boss 1054 out of the aperture of the main body 1002 unlocks the secondary body 1010 relative to the main body 1002 and allows the secondary body 1010 to slide or move axially within the main body 1002 so as to provide an indication of an applied anchor force.

FIG. 10D illustrates a cross section view of the epicardial anchor application device 1000 taken along line A-A of FIG. 10C. The cross sectional view illustrates various internal components of the epicardial anchor application device 1000. Specifically, FIG. 10D illustrates the spring component 1030 positioned within main body 1002. The spring component 1030 is configured to engage the proximal end of the secondary body 1010 and apply a spring force thereto. Specifically, the spring component 1030 includes a distal plug 1032 that engages the secondary body 1010 to transfer or provide the spring force to the secondary body 1010. The spring force is used in determining the force applied to the anchors by the epicardial anchor application device 1000. The cross sectional view also illustrates an inner shaft 1042 (FIG. 10E) positioned within the elongated shaft 1020. The inner shaft 1042 is movable or slidable within the elongated shaft 1020 to allow the pair of hooks 1022 and 1024 to move axially outward and inward relative to the elongated shaft 1020 and engagement pin 1025 and thereby lock and unlock the epicardial anchor as described below.

Figure 10E:
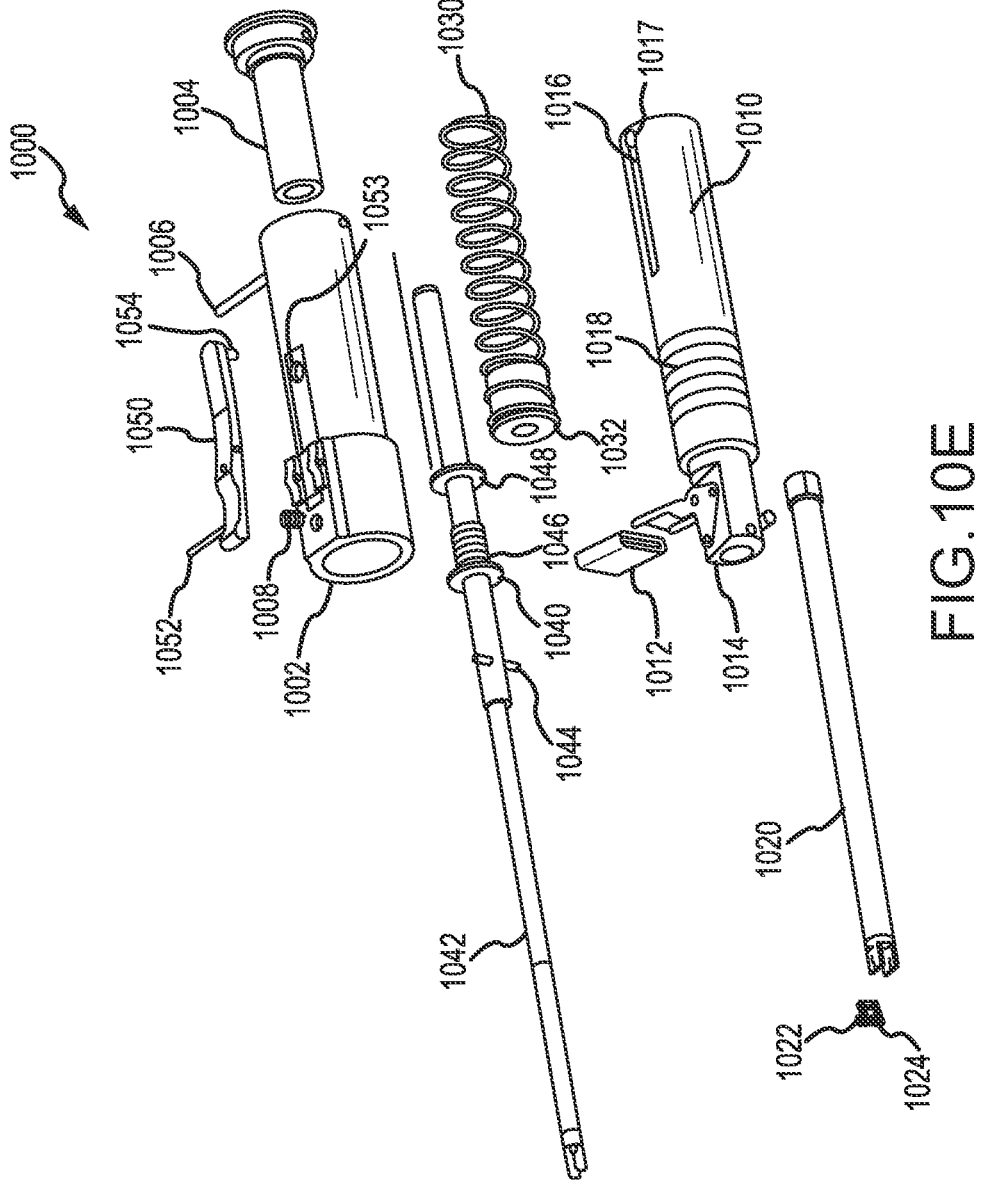
Figures 11A, 11B, 11C, 11D:
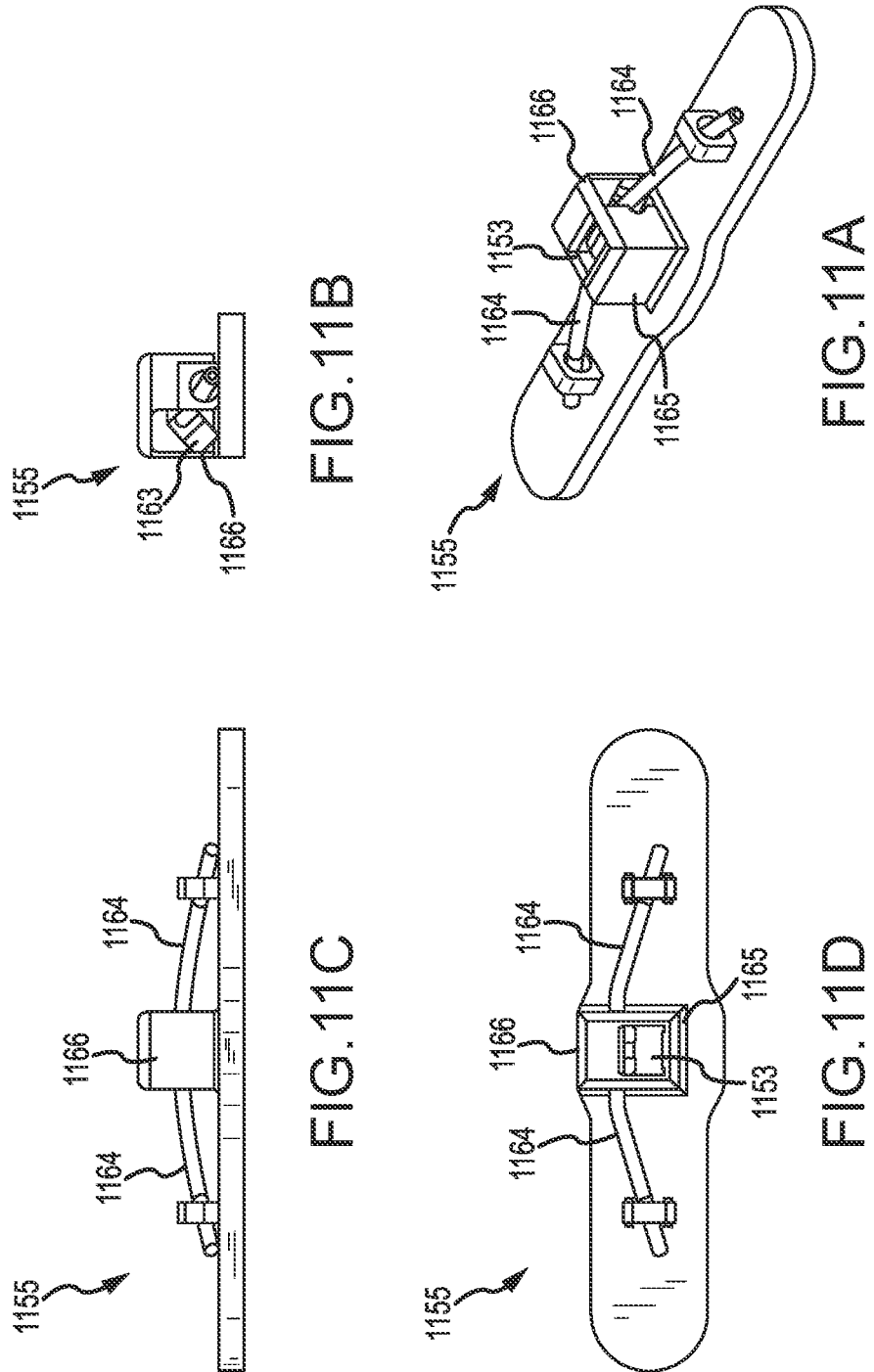

FIG. 10E illustrates an exploded perspective view of the components of epicardial anchor application device 1000. As shown in FIG. 10E, main body 1002 may be coupled with locking mechanism 1050 via a pin 1052 that allows the locking mechanism 1050 to pivot such that boss 1054 is able to pivot into and out of the aperture 1053 of main body 1002 as a user presses and releases a distal portion of the locking mechanism 1050. A spring 1008 may be positioned under the distal portion of the locking mechanism 1050 to bias the locking mechanism 1050 toward a locked position in which the boss 1054 is positioned within the aperture 1053 of main body 1002. The main body 1002 may also include a bottom plug 1004 that may be coupled with the main body 1002 via a pin 1006. The bottom plug 1004 provides a surface against which the spring component 1030 presses as the secondary body 1010 moves axially within the main body 1002.

To lock the secondary body 1010 relative to the main body 1002, the boss 1054 of locking component 1050 may engage with a groove or channel 1016 of secondary body 1010 when the boss 1054 is positioned within the aperture of main body 1002. Frictional contact between the boss 1054 and channel 1016 may prevent secondary body 1010 from moving axially within the main body 1002. In some embodiments, the secondary body 1010 may be locked relative to the main body 1002 in any axial position within main body 1002. In other embodiments, the secondary body 1010 may be locked relative to main body 1002 only in a fully extended position, such as by insertion of boss 1054 within an aperture 1017 positioned at a distal end of groove or channel 1016. In such embodiments, boss 1054 may slide along groove or channel 1016 to allow the secondary body 1010 to slide relative to main body 1002 until boss 1054 engages with aperture 1017. This embodiment may allow locking mechanism 1050 to be pressed only a single time to retract boss 1054 from aperture 1017 and position boss 1054 within groove or channel 1016 and thereby enable sliding of secondary body 1010 within main body 1002 until aperture 1017 is reengaged by boss 1054.

FIG. 10E further illustrates the lever mechanism 1012 that may be operated to lock and unlock an epicardial anchor. The lever mechanism 1012 may include a cap that softens a force or pressure exerted on the user's finger as the user operates lever mechanism 1012. The elongated shaft 1020 may be coupled with a distal end 1014 of secondary body 1010 using a set screw or any other known coupling mechanism in the art (e.g., adhesive bonding, welding, mechanically fastening, and the like). As described herein, a pair of hooks or arms, 1022 and 1024, are positioned at the distal end of the elongated shaft 1020. The elongated shaft 1020 includes a lumen within which an inner shaft 1042 is slidably disposed. The inner shaft 1042 includes a pin 1044 that couples with the lever mechanism 1012 to allow the inner shaft 1042 to slide proximately and distally within elongated shaft 1020 as the lever mechanism 1012 is operated by a user. A distal end of the inner shaft 1042 engages with the pair of hooks or arms, 1022 and 1024, to allow the hooks or arms to engage with an epicardial anchor and thereby lock and unlock the epicardial anchor about a tether as the lever mechanism 1012 is operated by a user.

The inner shaft 1042 also includes a pair of washers 1040 and 1048 that are used to align the components within the assembly. The inner shaft 1042 further includes a spring component 1046 that biases the inner shaft 1042 distally relative to the elongated shaft 1020 to ensure that the pair of hooks, 1022 and 1024, remain unlocked or disengaged from the epicardial anchor when the lever mechanism 1012 is in an unlocked or disengaged configuration. Stated differently, the spring component 1046 ensures that the pair of hooks 1022 and 1024 do not remain locked or engaged with the epicardial anchor when the lever mechanism is operated by a user to release the epicardial anchor.

FIGS. 11A-D illustrate an embodiment of an exemplary epicardial anchor 1155. As described herein, epicardial anchor 1155 may be coupled with a tension member or tether and advanced toward an external wall EW of the heart via an epicardial anchor application device or tensioning device, such as those illustrated in FIGS. 10A-E. Epicardial anchor 1155 includes a lumen 1153, through which a tether is inserted. Epicardial anchor 1155 has a spring cam structure 1163, which is more fully described in U.S. patent Publication No. US2010/0016655, entitled "Cardiac Anchor Structures, Methods, and Systems for treatment of Congestive Heart Failure and Other Conditions;" the full disclosures of which are incorporated herein by reference. The spring cam 1163 allows the epicardial anchor 1155 to slide along a tether toward a septal anchor that is positioned adjacent the septum, but inhibits sliding of the epicardial anchor 1155 away from the septal anchor. As such, the spring cam 1163 effectively maintains a tissue engagement force between the epicardial anchor 1155 and a septal anchor.

To engage the cam spring mechanism 1163 of epicardial anchor 1155, the epicardial anchor application device 1000 includes a pair of hooks, 1022 and 1024, that are positionable around a pair of arms 1164 of epicardial anchor 1155. The pair of arms 1164 are in turn connected to, or otherwise operationally coupled with, cam spring mechanism 1163. A rod (i.e., engagement rod 1025) may be positioned between the pair of hooks, 1022 and 1024, and may engage the cam spring mechanism 1163 to pivot the cam mechanism between a locked or engaged state and an unlocked or unengaged state. In operation, the pair of hooks, 1022 and 1024, may be clamped around arms 1164 so that housing 1165 is positioned between hooks 1022 and 1024. The lever mechanism 1012 may then be operated to retract the inner shaft 1042 and hooks, 1022 and 1024, at least partially within elongated shaft 1020 which causes the rod 1025 to contact and press against housing surface 1166. Operation of the lever mechanism 1012 forces the rod 1025 to push on housing surface 1166, which causes hooks 1022 and 1024 to pull on arms 1164, which in turn causes cam spring mechanism 1163 to rotate away from and/or out of contact with the tether of tension member (i.e., 412 of FIGS. 8F-H), thereby permitting epicardial anchor 1155 to slide both distally and proximally along tether 412 toward and away from the septal anchor (i.e., 410 of FIGS. 8G-I).

Similarly, the lever mechanism 1012 may be operated in a reverse manner to cause the inner shaft 1042 and hooks, 1022 and 1024, to extend from shaft 1020, which allows the arms 1164 to resiliently return to a position in which the cam rotates into contact with the tether 412, thereby inhibiting the epicardial anchor 1155 from sliding proximally along the tether and away from the septal anchor 410. Arms 1164 may function as a spring to bias the cam 1163 toward the tether 412 and lock epicardial anchor 1155 about the tether 412. The lever mechanism 1012 may be operated from outside the patient's body to lock the epicardial anchor 1155 relative to the tether 412 or unlock the epicardial anchor 1155 relative to the tether 412. In this manner, the epicardial anchor application device 1000 may be used to reconfigure the epicardial anchor 1155 between a variable force mode that allows the epicardial anchor 1155 to slide proximally and distally along the tether or tension member and a set force mode that restricts proximal movement of the epicardial anchor 1155 along the tether or tension member.

To more accurately apply septal/external wall engagement forces within a desired range, epicardial anchor application device 1000 can engage the cam spring mechanism 1163 of epicardial anchor 1155 to reconfigure the epicardial anchor 1155 into a variable force mode in which the anchor is free to slide in both axial directions along the tether 412. This allows a controlled force to be applied between the tether 412 and epicardial anchor 1155 despite a beating of the heart.

The applied anchor force may be an appropriate amount of force to bring external wall EW and septum S into engagement while preventing migration of the epicardial anchor 1155 and a septal anchor relative to external wall EW and septum S. For example, the force may be sufficient so that an inner surface of external wall EW and septum SE directly contact each other and so that epicardial anchor 1155 and a septal anchor are secured tightly about external wall EW and septum S, but not too strong to cause epicardial anchor 1155 and/or septal anchor to be pulled through and/or into external wall EW and/or septum S.

Referring now to FIG. 12, illustrated is a method for securing heart anchors of a heart implant device. At block 1210, a first anchor is positioned in engagement with a first wall of the heart. The first anchor is coupled with a tension member or tether as described herein. At block 1220, a second anchor is positioned in engagement with a second wall of the heart. The second anchor is slidably coupled with the tension member or tether such that the second anchor may slide proximally and distally along a length of the tension member. At block 1230, a tensioning device is advanced over the tension member so that a distal end of the tensioning device engages the second anchor while a main body of the tensioning device is positioned outside of the body. The tensioning device may be similar to any of the embodiments described herein, such as the epicardial anchor application device 1000 illustrated in FIGS. 10A-E. At block 1240, a desired anchor force is applied between the tension member and the second anchor via the tensioning device so that the first anchor provides a force urging the first wall toward the second wall and the second anchor provides a force urging the second wall toward the first wall. As described herein, the tensioning device provides an indication of the anchor force applied to the second anchor by the tensioning device. At block 1250, a locking mechanism of the tensioning device is actuated to secure the second anchor to the tension member to restrict proximal movement of the second anchor along the tension member.

In some embodiments, the locking mechanism of the tensioning device reconfigures the second anchor from a variable force mode that allows the second anchor to slide proximally and distally along the tension member to a set force mode that restricts proximal movement of the second anchor along the tension member, and vice versa. In some embodiments, actuating the locking mechanism of the tensioning device causes a pair of hooks to move axially relative to a pin positioned at a distal end of an elongated shaft of the tensioning device. Movement of the pair of hooks relative to the pin forces the pin into engagement with a cam component of the second anchor to lock and unlock the second anchor.

In some embodiments, the method also includes advancing the second anchor distally along the tension member with the tensioning device in a first mode of operation, the first mode of operation allowing the tensioning device to engage the second anchor to urge the second wall toward the first wall without indicating the anchor force being applied by the tensioning device, and applying the desired anchor force to the second anchor with the tensioning device in a second mode of operation, the second mode of operation allowing the tensioning device to provide the indication of the anchor force applied to the second anchor by the tensioning device. In some embodiments, the method may further include actuating a mode button of a main body of the tensioning device to switch the tensioning device from the first mode of operation to the second mode of operation. In some embodiments, the applied anchor force may include a Ventricular Contractile Force (VCF) and an additional force of between about 2 N and about 6 N. In other embodiments, the applied anchor force may include a Ventricular Contractile Force (VCF) and an additional force of between about 3 N and about 4 N.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a process" includes a plurality of such processes and reference to "the device" includes reference to one or more devices and equivalents thereof known to those skilled in the art, and so forth.

Also, the words "comprise," "comprising," "include," "including," and "includes" when used in this specification and in the following claims are intended to specify the presence of stated features, integers, components, or steps, but they do not preclude the presence or addition of one or more other features, integers, components, steps, acts, or groups.

The invention claimed is:

1. A method comprising:

providing a heart anchor positioning device including a device body and an elongated shaft slidingly positioned within the device body, the elongated shaft having a proximal end, a distal end, and a lumen extending between the proximal end and the distal end;

coupling the distal end of the elongated shaft to a heart anchor;

advancing the elongated shaft and the heart anchor over a tension member to position the heart anchor against an outer wall of a heart, wherein the tension member extends through the lumen of the elongate shaft;

applying a force to the heart anchor to urge the wall toward an opposite wall of the heart; and switching the heart anchor from a variable force mode in which the heart anchor is slidable along the tension member to a set force mode in which the heart anchor is inhibited from sliding along the tension member;

wherein the heart anchor positioning device provides an indication of the anchor force applied to the heart anchor during the variable force mode, and wherein the device body includes a handle and the method further comprises actuating a locking mechanism on the handle to switch the heart anchor from the variable force mode to the set force mode.

2. The method of claim 1, wherein the actuating the lock mechanism moves a hook relative to a pin positioned at the distal end of the elongate shaft, and wherein movement of the hook relative to the pin causes a cam component of the heart anchor to engage the tension member.

3. The method of claim 1, further comprising actuating a button component of the device body to switch the elongated shaft from being locked to unlocked with respect to the movement relative to the device body.

4. The method of claim 1, wherein the anchor force comprises a Ventricular Contractile Force (VCF) and an additional force of between 2 N and 6 N.

5. The method of claim 1, further comprising disengaging the distal end of the elongated shaft from the heart anchor and withdrawing the elongated shaft over the tension member.

6. The method of claim 1, wherein the elongated shaft is operably coupled with a spring component positioned within the device body, and the method further comprises the spring component biasing the elongated shaft toward a fully deployed position relative to the device body.

7. A method comprising:

positioning a first heart anchor into engagement with a first wall of the heart of a patient;

sliding a second heart anchor along the tension line by pushing the second heart anchor a distal end of an elongated shaft through which extends the tension line, wherein the sliding positions the second heart anchor against a second wall of the heart;

during the sliding, the pushing applies a force to the heart anchor to urge the second wall toward the first wall of the heart;

during the sliding, providing an indication of the force applied to the second heart anchor wherein the indication is provided by a device body to which the external shaft is attached and is external to the patient; and actuating a lock mechanism at the device body to secure the second heart anchor to the tension member to restrict proximal movement of the heart anchor along the tension member, wherein the actuating the lock mechanism moves a pin on the distal end of the elongated shaft and the pin pushes a cam on the second heart anchor to latch the tension member.

8. The method of claim 7, wherein the applied anchor force comprises a Ventricular Contractile Force (VCF) and an additional force comprises a force of between 2 N and 6 N.

9. The method of claim 7, further comprising disengaging the distal end of the elongated shaft from the heart anchor and withdrawing the elongated shaft over the tension member.

10. The method of claim 7, wherein the elongated shaft is operably coupled with a spring component positioned within the device body, and the method further comprises the spring component biasing the elongated shaft toward a fully deployed position relative to the device body.

11. A method to implant heart anchors positioning system comprising:

pulling a tension line through a first wall and a second wall of a heart;

seating a first heart anchor attached to a distal end of the tension line on the first wall by the pulling of the tension line;

attaching a second heart anchor to a distal end of an elongated shaft including a lumen through which extends the tension line, wherein the distal end of the elongated shaft releasably engages the second heart anchor;

manually applying a force to a handle attached to a proximal end of the elongated shaft to advance the elongated shaft and the second heart anchor along the tension line such that distal end pushes the second heart anchor against the second wall of the heart and urges the second wall toward the first wall, and latching the second heart anchor on the tension line and releasing the second heart anchor from the distal end of the elongated shaft while the second anchor is against the second wall and the second wall is urged toward the first wall, wherein the latching and the releasing are actuated by at least one manual action applied to the handle.

12. The method of claim 11, further comprising providing at the handle an indication of the force applied to the handle to push the second heart anchor against the first wall.

13. The method of claim 11, wherein the first wall is a septal wall of the heart and the second wall is an outer wall of the heart.

14. The method of claim 11, wherein the pulling of the tension line pulls the tension line through a left ventricle of the heart.

15. The method of claim 11, wherein the latching the second heart anchor includes actuating a cam component on the second heart anchor by the at least one manual action applied to the handle.

16. The method of claim 11, wherein the latching includes moving a pin protruding from the distal end axially relative to the elongated shaft axially to actuate a cam on the second heart anchor to cause the second heart anchor to latch on the tension line.

17. The method of claim 16, wherein the moving of the pin is caused by moving a lever on the handle.

18. The method of claim 17, wherein the elongated shaft includes an inner shaft and an outer shaft, and wherein the inner shaft is axially moveable relative to the outer shaft by operation in response to actuation of the lever mechanism, wherein axial movement of the inner shaft relative to the outer shaft moves the pin axially relative to the hook member.

\* \* \* \* \*

28